United States Patent
Marshall

(10) Patent No.: US 7,824,346 B2
(45) Date of Patent: Nov. 2, 2010

(54) DETERMINING CONDYLE DISPLACEMENT UTILIZING ELECTRONIC MODELS OF DENTAL IMPRESSIONS HAVING A COMMON COORDINATE SYSTEM

(75) Inventor: Michael Craig Marshall, Prior Lake, MN (US)

(73) Assignee: Geodigm Corporation, Chanhassen, MN (US)

( * ) Notice: Subject to any disclaimer, the term of this patent is extended or adjusted under 35 U.S.C. 154(b) by 1086 days.

(21) Appl. No.: 11/231,064

(22) Filed: Sep. 19, 2005

(65) Prior Publication Data
US 2006/0095242 A1    May 4, 2006

Related U.S. Application Data

(63) Continuation-in-part of application No. 10/799,344, filed on Mar. 11, 2004, now Pat. No. 7,702,492.

(51) Int. Cl.
| | |
|---|---|
| A61B 5/103 | (2006.01) |
| A61B 5/117 | (2006.01) |
| A61C 19/04 | (2006.01) |
| G01C 9/00 | (2006.01) |
| G01C 17/00 | (2006.01) |
| G01C 19/00 | (2006.01) |

(52) U.S. Cl. .............. 600/590; 600/587; 600/595; 433/68; 433/69; 702/153

(58) Field of Classification Search .......... 600/300, 600/587, 589, 590, 595; 433/2, 24, 68, 69, 433/70, 71; 702/19, 150, 151, 152, 153; 128/920, 922, 923; 382/100, 110, 128, 130, 382/131, 132

See application file for complete search history.

(56) References Cited

U.S. PATENT DOCUMENTS

| | | | |
|---|---|---|---|
| 3,084,438 A | 4/1963 | Goodfriend |
| 4,123,768 A | 10/1978 | Kilshaw et al. |
| 4,123,786 A | 10/1978 | Cramer |
| 4,182,312 A | 1/1980 | Mushabac |
| 4,402,326 A | 9/1983 | Okano et al. |

(Continued)

FOREIGN PATENT DOCUMENTS

IS    120867    5/1997

(Continued)

OTHER PUBLICATIONS

Travers et al., "Associations between incisor and mandibular condylar movements during maximum mouth opening in humans." *Archives of Oral Biology* 45(2000): 267-275.

(Continued)

*Primary Examiner*—Jeffrey G Hoekstra
(74) *Attorney, Agent, or Firm*—Merchant & Gould P.C.

(57) ABSTRACT

A system and method for determining condyle displacement during jaw articulation includes a physical model with corresponding reference points. The physical model is positioned and scanned to obtain positional data representing a first and second bite position. This positional data is used to generate a transformation matrix. The position of at least one condyle is determined in reference to positional data scanned from the physical model. The transformation matrix is used to map the position of the condyle with respect to the second bite position.

11 Claims, 18 Drawing Sheets

U.S. PATENT DOCUMENTS

| | | |
|---|---|---|
| 4,436,684 A | 3/1984 | White |
| 4,575,805 A | 3/1986 | Moermann et al. |
| 4,611,288 A | 9/1986 | Duret et al. |
| 4,673,352 A | 6/1987 | Hansen |
| 4,742,464 A | 5/1988 | Duret et al. |
| 4,752,964 A | 6/1988 | Okada et al. |
| 4,775,946 A | 10/1988 | Anjyo |
| 4,799,785 A | 1/1989 | Keates et al. |
| 4,837,732 A | 6/1989 | Brandestini et al. |
| 4,862,371 A | 8/1989 | Maekawa |
| 4,862,391 A | 8/1989 | Ohhashi |
| 4,935,635 A | 6/1990 | O'Harra |
| 4,983,120 A | 1/1991 | Coleman et al. |
| 5,020,993 A | 6/1991 | Levandoski |
| 5,027,281 A | 6/1991 | Rekow et al. |
| 5,113,424 A | 5/1992 | Burdea et al. |
| 5,121,333 A | 6/1992 | Riley et al. |
| 5,150,457 A | 9/1992 | Behm et al. |
| 5,184,306 A | 2/1993 | Erdman et al. |
| 5,198,827 A | 3/1993 | Seaton |
| 5,198,877 A | 3/1993 | Schulz |
| 5,224,049 A | 6/1993 | Mushabac |
| 5,257,184 A | 10/1993 | Mushabac |
| 5,257,203 A | 10/1993 | Riley et al. |
| 5,267,293 A | 11/1993 | Virta |
| 5,273,429 A | 12/1993 | Rekow et al. |
| 5,320,528 A | 6/1994 | Alpern et al. |
| 5,338,198 A | 8/1994 | Wu et al. |
| 5,340,309 A | 8/1994 | Robertson |
| 5,343,391 A | 8/1994 | Mushabac |
| 5,347,454 A | 9/1994 | Mushabac |
| 5,359,511 A | 10/1994 | Schroeder et al. |
| 5,368,478 A | 11/1994 | Andreiko et al. |
| 5,372,502 A | 12/1994 | Massen et al. |
| 5,395,238 A | 3/1995 | Andreiko et al. |
| 5,416,822 A | 5/1995 | Kunik |
| 5,431,562 A | 7/1995 | Andreiko et al. |
| 5,440,393 A | 8/1995 | Wenz |
| 5,442,572 A | 8/1995 | Kiridena et al. |
| 5,447,432 A | 9/1995 | Andreiko et al. |
| 5,448,472 A | 9/1995 | Mushabac |
| 5,454,068 A | 9/1995 | Ramanujam |
| 5,454,717 A | 10/1995 | Andreiko et al. |
| 5,458,487 A | 10/1995 | Komatsu et al. |
| RE35,169 E | 3/1996 | Lemchen et al. |
| 5,518,397 A | 5/1996 | Andreiko et al. |
| 5,533,895 A | 7/1996 | Andreiko et al. |
| 5,549,476 A | 8/1996 | Stern |
| 5,562,448 A | 10/1996 | Mushabac |
| 5,569,578 A | 10/1996 | Mushabac |
| 5,588,430 A | 12/1996 | Bova et al. |
| 5,605,459 A | 2/1997 | Kuroda et al. |
| 5,683,243 A | 11/1997 | Andreiko et al. |
| 5,730,151 A | 3/1998 | Summer et al. |
| 5,800,174 A | 9/1998 | Anderson |
| 5,823,778 A | 10/1998 | Schmitt et al. |
| 5,842,858 A | 12/1998 | Truppe |
| 5,879,158 A | 3/1999 | Doyle et al. |
| 5,880,962 A | 3/1999 | Andersson et al. |
| 5,882,192 A | 3/1999 | Bergersen |
| 5,905,658 A | 5/1999 | Baba |
| 5,977,979 A | 11/1999 | Clough et al. |
| 5,989,199 A | 11/1999 | Cundari et al. |
| 6,015,289 A | 1/2000 | Andreiko et al. |
| 6,068,482 A | 5/2000 | Snow |
| 6,123,544 A | 9/2000 | Cleary |
| 6,143,003 A | 11/2000 | Cosman |
| 6,152,731 A | 11/2000 | Jordan et al. |
| 6,217,334 B1 | 4/2001 | Hultgren |
| 6,227,850 B1 | 5/2001 | Chishti et al. |
| 6,244,861 B1 | 6/2001 | Andreiko et al. |
| 6,250,918 B1 | 6/2001 | Sachdeva et al. |
| 6,318,994 B1 | 11/2001 | Chishti et al. |
| 6,322,359 B1 | 11/2001 | Jordan et al. |
| 6,322,728 B1 | 11/2001 | Brodkin et al. |
| 6,334,853 B1 | 1/2002 | Kopelman et al. |
| 6,364,660 B1 | 4/2002 | Durbin et al. |
| 6,371,761 B1 | 4/2002 | Cheang et al. |
| 6,406,292 B1 | 6/2002 | Chishti et al. |
| 6,409,504 B1 | 6/2002 | Jones et al. |
| 6,436,684 B1 | 8/2002 | Woodage et al. |
| 6,450,807 B1 | 9/2002 | Chisti et al. |
| 6,471,511 B1 | 10/2002 | Chishti et al. |
| 6,554,613 B1 | 4/2003 | Sachdeva et al. |
| 6,579,095 B2 | 6/2003 | Marshall et al. |
| 6,602,070 B2 | 8/2003 | Miller et al. |
| 6,608,628 B1 | 8/2003 | Ross et al. |
| 6,611,617 B1 | 8/2003 | Crampton |
| 6,632,089 B2 | 10/2003 | Rubbert et al. |
| 6,648,640 B2 | 11/2003 | Rubbert et al. |
| 6,688,886 B2 | 2/2004 | Hughes et al. |
| 6,726,478 B1 | 4/2004 | Isiderio et al. |
| 6,772,026 B2 | 8/2004 | Bradbury et al. |
| 6,783,360 B2 | 8/2004 | Chishti |
| 6,905,337 B1 | 6/2005 | Sachdeva |
| 6,925,198 B2 | 8/2005 | Scharlack et al. |
| 7,200,642 B2 | 4/2007 | Hultgren et al. |
| 7,215,803 B2 | 5/2007 | Marshall |
| 7,347,686 B2 | 3/2008 | Marshall |
| 7,362,890 B2 | 4/2008 | Scharlack et al. |
| 7,474,307 B2 | 1/2009 | Chishti et al. |
| 2001/0002310 A1 | 5/2001 | Chishti et al. |
| 2002/0015934 A1 | 2/2002 | Rubbert et al. |
| 2002/0031743 A1 | 3/2002 | Kim |
| 2002/0081554 A1* | 6/2002 | Marshall et al. ............. 433/213 |
| 2003/0224316 A1 | 12/2003 | Marshall |
| 2004/0015327 A1 | 1/2004 | Sachdeva et al. |
| 2004/0023183 A1 | 2/2004 | Miller et al. |
| 2004/0066877 A1 | 4/2004 | Arai et al. |
| 2004/0110110 A1 | 6/2004 | Chishti et al. |
| 2005/0019721 A1 | 1/2005 | Chishti |
| 2005/0028826 A1 | 2/2005 | Palmisano |
| 2005/0095562 A1 | 5/2005 | Sporbert et al. |
| 2005/0153255 A1 | 7/2005 | Sporbert et al. |
| 2005/0271996 A1 | 12/2005 | Sporbert et al. |
| 2008/0002869 A1 | 1/2008 | Scharlack et al. |

FOREIGN PATENT DOCUMENTS

| | | |
|---|---|---|
| IS | 120892 | 5/1997 |
| IS | 121872 | 9/1997 |
| WO | WO 98/32394 A1 | 7/1998 |

OTHER PUBLICATIONS

Alcaniz, M. et al., "An Advanced System for the Simulation and Planning of Orthodontic Treatment," *Medical Image Analysis*, vol. 2, No. 1, pp. 61-77 (Mar. 1998) (1 page abstract).

Alcaniz, M. et al., "A System for the Simulation and Planning of Orthodontic Treatment Using a Low Cost 3D Laser Scanner for Dental Anatomy Capturing," *Studies in Health Technology and Informatics*, vol. 62, pp. 8-14 (1999) (1 page abstract).

Andrews, L., "The six keys to normal occlusion," *American Journal of Orthodontics*, vol. 62, No. 3, cover page, table of contents, and pp. 296-309 (Sep. 1972).

Baker, H., "Building, Visualizing, and Computing on Surfaces of Evolution," *IEEE Computer Graphics and Applications*, cover page and pp. 31-41 (Jul. 1988).

Hayashi, T. et al., "A Computerized System for Analyzing Occlusal Relations During Mandibular Movements," *The International Journal of Prosthodontics*, vol. 7, No. 2, cover page and pp. 108-114 (Mar./Apr. 1994).

Hibi, H. et al., "An Optical System for Measuring Inclination and area of Occlusal Facets," *Journal of Oral Rehabilitation*, vol. 24, No. 9, pp. 673-677 (Sep. 1997).

Jones, M. et al., "A Validated Finite Element Method Study of Orthodontic Tooth Movement in the Human Subject," *Journal of Orthodontics*, vol. 28. No. 1, pp. 29-38 (Mar. 2001) (1 page abstract).

Kimura, H. et al., "Three-Dimensional Shape Measurement of Teeth. On the Measurement by the Laser Displacement Meter which is able to Move on Z-direction," *Journal of the Japanese Society for Dental Materials and Devices*, vol. 8, No. 6, pp. 877-882 (Nov. 1989) (1 page abstract).

Kimura, H. et al., "Three-Dimensional Shape Measurement of Teeth. Measurement of Tooth Model by Tilting Method by Means of the Double Sensor Laser Displacement Meter, and the Simulation of Occlusion," *Journal of the Japanese Society for Dental Materials and Devices*, vol. 9, No. 4, pp. 679-686 (Jul. 1990) (1 page abstract).

Kunii, T. et al., "Articulation Simulation for an Intelligent Dental Care System," *University of Aizu*, vol. 15, No. 3, pp. 181-188 (1994).

Kuroda, T. et al., "Three-dimensional dental cast analyzing system using laser scanning," *American Journal of Orthodontics and Dentofacial Orthopedics*, vol. 110, No. 4, cover page, table of contents, and pp. 365-369 (Oct. 1996).

Larkin, J., "Means for measuring the interocclusal distance," *The Journal of Prosthetic Dentistry*, vol. 17, No. 3, pp. 247-250 (Mar. 1967).

Laurendeau, D. et al., "A Computer-Vision Technique for the Acquisition and Processing of 3-D Profiles of Dental Imprints: An Application in Orthodontics," *IEEE Transactions on Medical Imaging*, vol. 10, No. 3, pp. 453-461 (Sep. 1991).

Leinfelder, K. et al., "A new method for generating ceramic restorations: a CAD-CAM System," *Journal of the American Dental Association*, vol. 118, cover page and pp. 703-707 (Jun. 1989).

OrthoCad, "Virtual Set-Up," OrthoCad advertisement, 1 page (admitted by Applicants as prior art as of the filing date).

Palmer, R. "CAD/CAM Dental Technology's Future?," *Dental Lab Products*, pp. 14-18 (May/Jun. 2002).

Rekow, D., "Computer-aided design and manufacturing in dentistry; a review of the state of the art," *The Journal of Prosthetic Dentistry*, vol. 58, No. 4, cover page and pp. 513-516 (Oct. 1987).

Rodger, J. et al., "Choosing Rendering Parameters for Effective Communication of 3d Shape," *IEEE Computer Graphics and Applications*, pp. 20-28 (Mar./Apr. 2000).

Sakaguchi, R. et al., "Digital Imaging of Occlusal Contacts in the Intercuspal Position," *Journal of Prosthodontics*, vol, 3, No. 4, pp. 193-197 (Dec. 1994).

Santler, G. et al., "Indications and Limitations of Three-Dimensional Models in Cranio-Maxillofacial Surgery," *Journal of Cranial-Maxillo-Facial Surgery*, vol. 26, No. 1, pp. 11-16 (Feb. 1998) (1 page abstract).

Schirmer, U. et al., "Manual and Computer-Aided Space Analysis: A Comparative Study," *American Journal of Orthodontics and Dentofacial Orthopedics*, vol. 112, No. 6, pp. 676-680 (Dec. 1997) (1 page abstract).

Siirilä, H. et al., "A Photographic Method for Measuring Interocclusal Clearance," *Suom. Hammaslääk., Toim.* vol. 66, No. 3, pp. 177-182 (1970), English Summary, p. 181.

Tekscan, The T-Scan II "The Future Force in Occlusal Diagnostics", Online Tekscan System brochure, Retrieved from http://www.tekscan.com/dental/system.html, pp. 1-9 (Oct. 3, 2002).

Tekscan, T-Scan II "Dental Division Overview", Online Tekscan System brochure, Retrieved from http://tekscan.com/dental.html, pp. 1-2, (Oct. 3, 2002).

M. Naeije et al., OKAS-3D: Optoelectronic Jaw Movement Recording System with Six Degrees of Freedom; Medical & Biological Engineering & Computing, Sep. 1995, 33, 683-688.

Wenzel et al., "Accuracy of caries diagnosis in digital images from charge-coupled device and storage phosphor systems: an in vitro study," *Dentomaxilofac. Radiol*.(1995) 24 (4): 250-254.

Sohmura et al., "Use of CAD/CAM system to fabricate dental prostheses. Part 1: CAD for a clinical crown restoration," *The International Journal of Prosthodontics* (1995) 8 (3): 252-258.

Seymour et al., "Assessment of shoulder dimensions and angles of porcelain bonded to metal crown preparations," *The Journal of Prosthetic Dentistry* (1996) 75: 406-411.

Deng et al., "Occlusal contact changes before and after orthodontic treatment of a group of child & adolescent patients with TMJ disturbance," *Australian Orthodontic Journal* (1995) 13 (4): 231-237.

\* cited by examiner

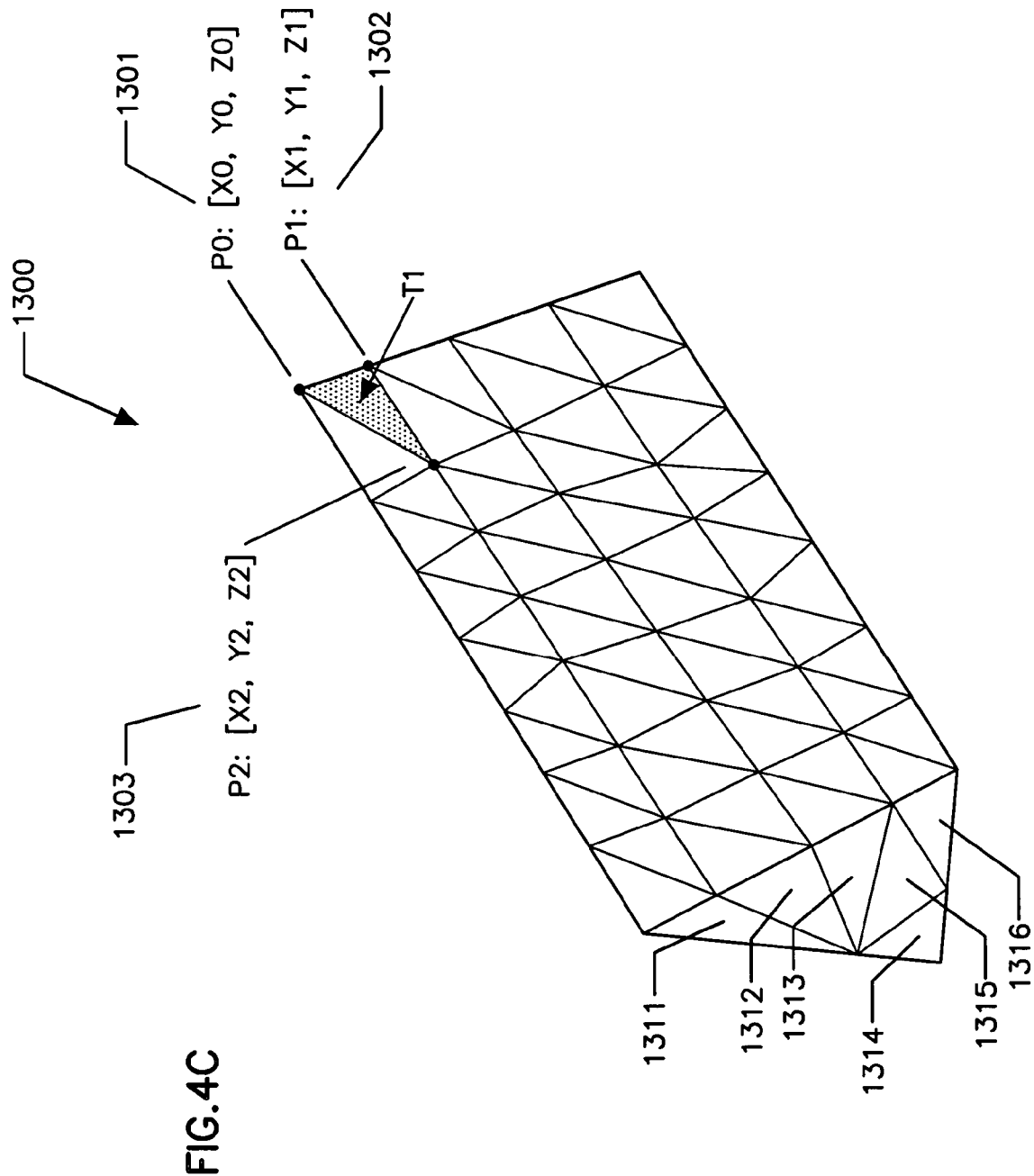

DETERMINING CONDYLE DISPLACEMENT UTILIZING ELECTRONIC MODELS OF DENTAL IMPRESSIONS HAVING A COMMON COORDINATE SYSTEM

RELATED APPLICATIONS

This application is a continuation-in-part of U.S. patent application Ser. No. 10/799,344, entitled, "SYSTEM AND METHOD FOR GENERATING AN ELECTRONIC MODEL FOR A DENTAL IMPRESSION HAVING A COMMON COORDINATE SYSTEM," filed Mar. 11, 2004 now U.S. Pat. No. 7,702,492. Such application is incorporated herein by reference.

TECHNICAL FIELD

This application relates in general to a method and system for determining condyle displacement during jaw articulation, and more particularly to a method and system for generating a transformation matrix to map the condyle position in various bite positions.

BACKGROUND

The use of computer-aided manipulating of electronic models that correspond to physical models has become more prevalent as the capabilities of computer processing systems have increased. One such application of this electronic modeling technology is in the dental field in which electronic models are generated that correspond to physical models made from impressions of teeth and gums in a human mouth. Dentists and other dental health professionals have used these physical models for a patient's teeth to study the interaction of the opposing jaws of the patient. In particular, the models may be used before, during, and after a treatment plan is implemented.

One application of this electronic modeling technology is in measuring the shift in position of a patient's left and right mandibular condyles caused by movement of the mandible. The mandibular condyles are the rounded prominences at the end of the mandible used for articulation with the maxilla. For convenience, each condyle may be thought of as defining a point of rotation for the mandible and maxilla. However, the mandible and maxilla do not interact in a strictly hinge-like fashion, rotating about a fixed point. Rather, during jaw articulation, in which the mandible moves with respect to the maxilla, each condyle shifts with respect to its original position and/or the other condyle. Taking this shift in position into account when creating a treatment plan enables the professional to tailor the plan to better suit the actual physical structure and characteristics of the patient.

FIGS. 1a-1b and 2a-2d illustrate various examples of condyle displacement during jaw articulation. Throughout these figures, the labels CR and CL refer to the right and left condyle respectively. The subscript "O" indicates an open mouth position, whereas the subscript "C" indicates a closed mouth position. As these figures show, the positions of each condyle CR, CL can change during jaw articulation. Referring now to FIGS. 1a-1b, one example of condyle displacement during jaw articulation is shown. FIG. 1a illustrates a front view of a patient's jaw in an open mouth position, depicting the left and right condyle positions $CR_O$, $CL_O$. A straight line between the two condyles CR, CL is shown to better illustrate the movement of each condyle in relation to the other. FIG. 1b illustrates a front view of a patient's jaw in a closed mouth position, depicting the left and right condyle positions $CR_C$, $CL_C$. In FIG. 1b, both condyles CR, CL have shifted slightly from their corresponding open mouth positions $CR_O$, $CL_O$.

FIGS. 2a-2d depict other possible examples of condyle displacement during jaw articulation. FIG. 2a depicts a first example E1 in which no displacement occurs during jaw articulation. FIG. 2b depicts another example E2 in which a lateral shift occurs for both condyles CR, CL during jaw articulation. FIG. 2c depicts yet another example E3 in which the left condyle CL shifts drastically with respect to the right condyle CR while the right condyle CR does not shift. FIG. 2d depicts yet another example E4 in which the left condyle CL shifts less drastically in one direction and the right condyle CR shifts less drastically in the opposite direction. However, while neither condyle CR, CL shifts very far between open and closed mouth positions, the resulting total condyle shift between the right condyle CR and the left condyle CL is just as drastic as in FIG. 2c.

One known method to measure condyle displacement for an individual patient includes a dental or orthodontic professional estimating the movement of each condyle based on a tactile observation of the shift. Another known method includes using a face bow to measure the distance between a condyle and a point on the patient's face while the patient holds her jaw in various positions. As will be appreciated, such methods are prone to error of a user in judging the magnitude or direction of the displacement.

Therefore, there arises a need in the art for a more accurate method, apparatus, and system to measure condyle displacement (i.e., or movement) for a patient.

SUMMARY OF THE INVENTION

This application relates in general to a method and system for determining mandibular condyle displacement during jaw articulation for a patient. The invention enables a user to measure the magnitude and direction of a shift in a patient's left and/or right mandibular condyle caused by movement of the patient's mandible in relation to the maxilla during jaw articulation. The following embodiments are constructed in accordance with the principles of the invention, but do not constitute the invention itself. Rather, the invention is defined in the claims attached hereto.

The method generally includes determining a transformation matrix from a first and second set of positional data, determining a location of a point corresponding to the condyle in relation to the first set of positional data, and transforming the point to the location of the condyle in relation to the second set of positional data using the transformation matrix. The first and second sets of positional data represent the patient's mandible, maxilla, or both in a first and second bite position, respectively.

According to one embodiment, creating a transformation matrix includes determining the location of at least three points in relation to either the mandible or the maxilla when the mandible and maxilla are interacting according to a first bite position. Creating the matrix further includes determining the location of the same three or more points when the mandible and maxilla are interacting according to a second bite position. The transformation matrix is generated based on the positional data of the three points taken in both bite positions.

According to another embodiment, positional data for intermediate positions of the mandible and maxilla between the two bite records may be interpolated, thereby showing jaw articulation in more detail. Position points for the condyle may also be shown for each of these intermediate positions.

According to yet another embodiment, a first and second electronic model is generated based on the positional data sets representing the mandible and maxilla, respectively. The determined and transformed condyle position points are displayed in relation to the electronic model.

According to still yet another possible embodiment, determining the positional data sets includes scanning a physical model including a base, at least a portion of a dental arch on one side of the base, and at least three reference sites on an opposite side of the base.

One aspect of the present invention includes generating an electronic model including the electronic model representing the mandible and the electronic model representing the maxilla on a common coordinate system.

Another aspect of the present invention includes determining a position of the condyle based on medical images. In some embodiments, a user determines the condyle point based on a visual interpretation of the medical image. In other embodiments, a software program determines the condyle point.

While the invention will be described with respect to preferred embodiment configurations and with respect to particular structures used therein, it will be understood that the invention is not to be construed as limited in any manner by either such configurations or structures described herein. Further, it will be appreciated that the present invention need not include each and every one of the features described herein. Instead, methods and assemblies constructed in accordance with the principles of the present invention may utilize one or more of the identified features.

BRIEF DESCRIPTION OF THE DRAWINGS

FIGS. 4A-4D illustrate the generation of electronic models from scanned data points of physical models;

DETAILED DESCRIPTION OF THE PREFERRED EMBODIMENT

Figure 1A:
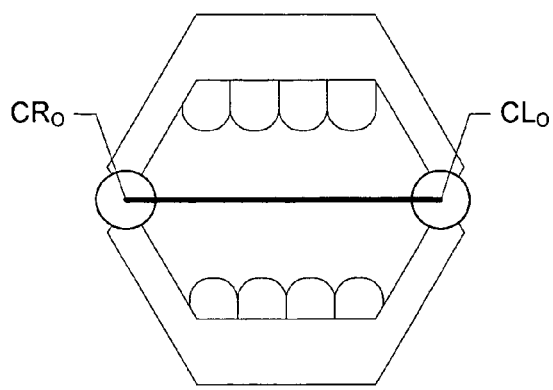
FIGS. 1a-1b illustrate one example of condyle displacement during jaw articulation.
Figure 1B:
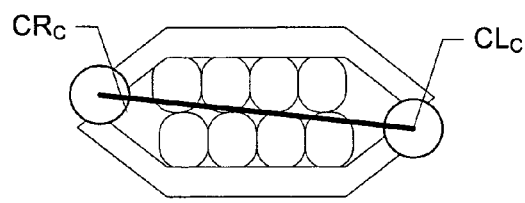
Figure 2A:
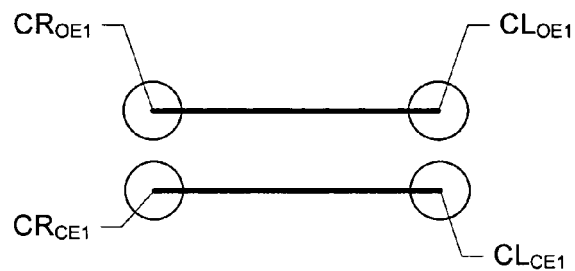
FIGS. 2a-2d illustrate various other examples of condyle displacement during jaw articulation.
Figure 2B:
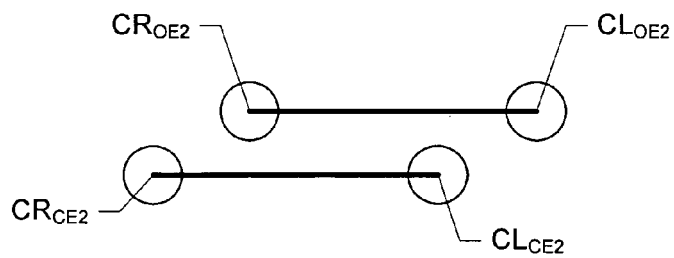
Figure 2C:
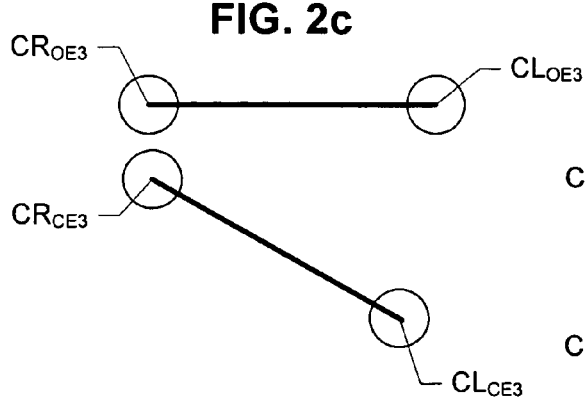
Figure 2D:
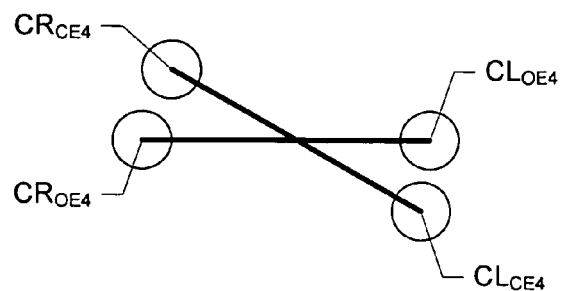

This application relates in general to a method and apparatus for determining condyle displacement during jaw articulation for a patient. In the following detailed description of exemplary embodiments of the invention, reference is made to the accompanying drawings, which form a part hereof, and which is shown by way of illustration, specific exemplary embodiments of which the invention may be practiced. These embodiments are described in sufficient detail to enable those skilled in the art to practice the invention, and it is to be understood that other embodiments may be utilized, and other changes may be made, without departing from the spirit or scope of the present invention. The following detailed description is, therefore, not to be taken in a limiting sense, and the scope of the present invention is defined only by the appended claims.

Throughout the specification and claims, the following terms take the meanings explicitly associated therein, unless the context clearly dictates otherwise. Referring to the drawings, like numbers indicate like parts throughout the views.

Figure 3:
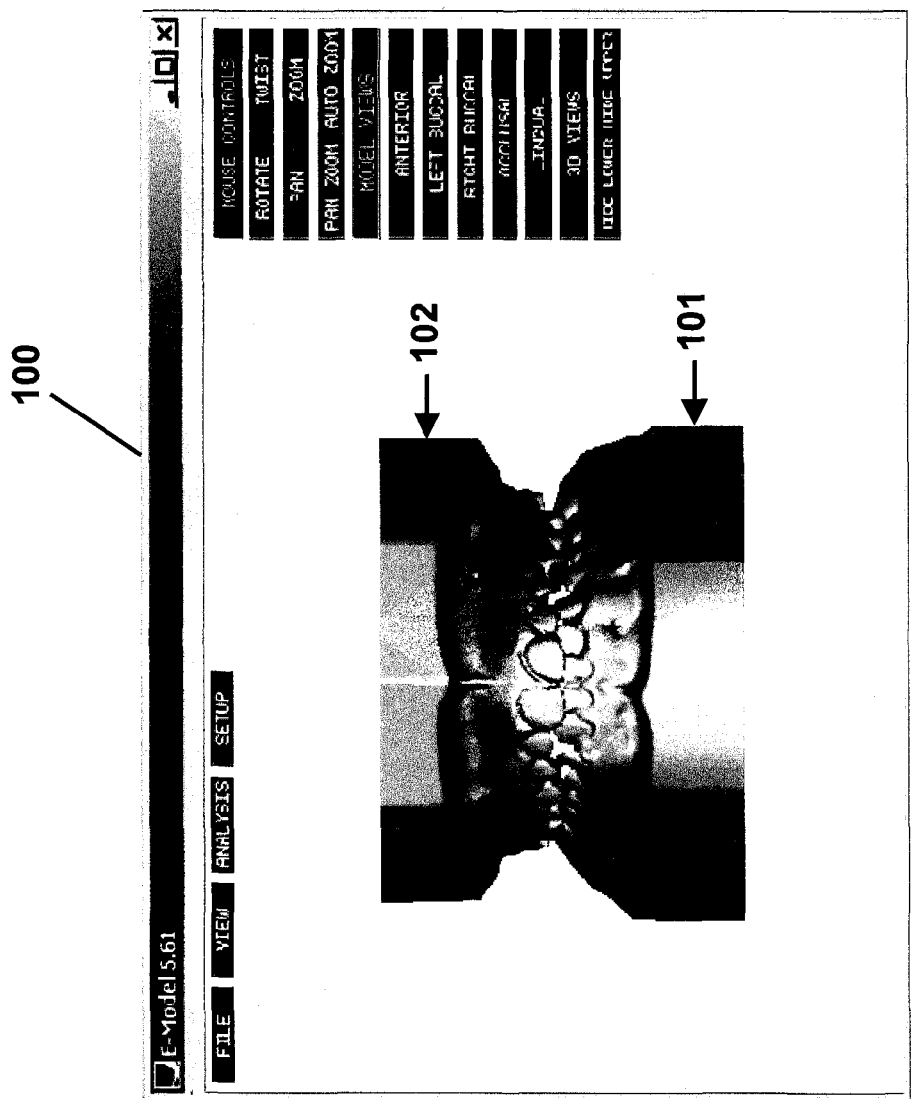
FIG. 3 illustrates one example embodiment of a composite electronic model including a first and a second electronic model.

Turning to FIG. 3, one example embodiment of a computer-generated image 100 of a composite electronic model 103 includes a first and a second electronic model 101, 102. The electronic models 101, 102 correspond to physical models 201, 202 (best seen in FIG. 8) of a patient's mandible and maxilla, respectively. In one embodiment, the two models 101, 102 are generated separately, combined into a common coordinate system, and positioned together to demonstrate the interaction of the opposing teeth present on the maxilla and the mandible. Interaction of other points known relative to at least one of the electronic models 101, 102, a condyle for example, can also be displayed.

Figure 4A:
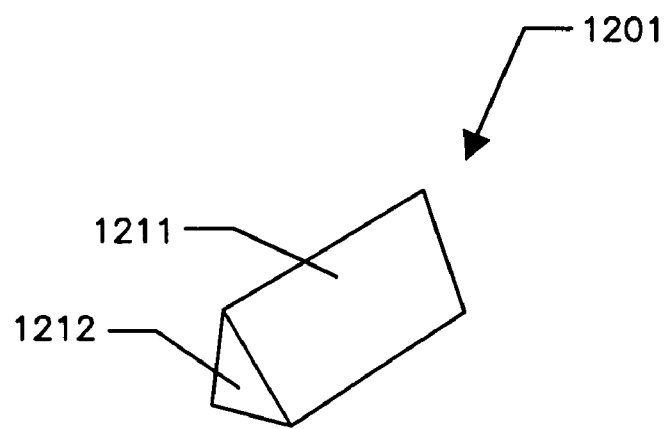
Figure 4B:
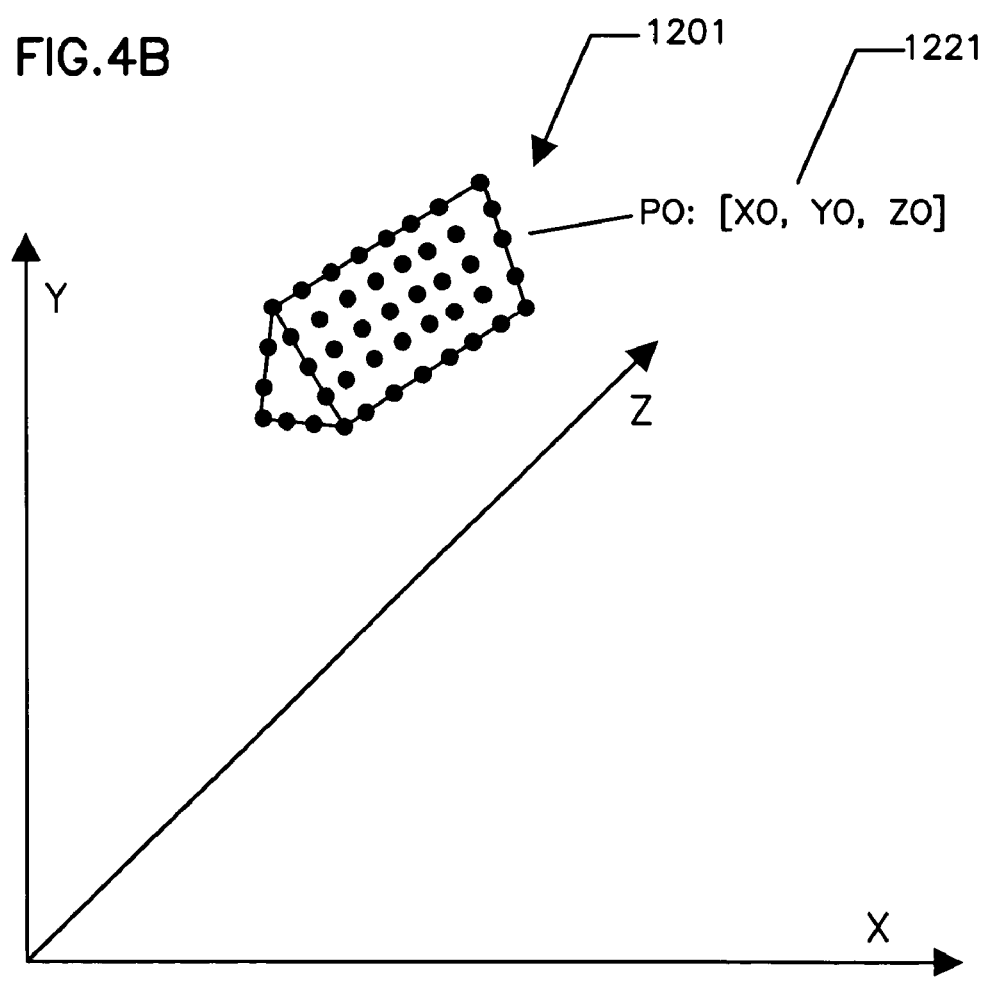

Referring now to FIGS. 4A-4D, the generation of electronic models from scanned data points of physical models will be briefly described. When a laser line scanning device or other suitable scanner passes a sensor over a surface of a physical model, a line of points corresponding to the position of the model's surface is obtained. In FIGS. 4A-4B, data points 1221 of a first and second surface 1211, 1212 of a physical object 1201 are specified using a three coordinate position P={X, Y, Z}. As the laser is moved within a scanning area of a multi-axis platform, the scanning device translates the data points 1221 to a coordinate system of the scanning device such that the collection of all points represents the points in a 3D coordinate system that corresponds to the surfaces 1211, 1212 of the model 1201. These data points 1221 are stored within a point cloud data file. It will be appreciated that only a first data point 1221 is explicitly shown as Po in FIG. 4B. However, a plurality of undesignated points is illustrated. Each of the other points may be identified as described in connection with FIG. 4C below.

Referring now to FIG. 4C, the point cloud data file is reduced to an original polygonal mesh 1300 of triangles in which the surfaces of the triangles are used to approximate the surfaces 1211, 1212 of the physical model 1201. Each triangle in the original polygonal mesh 1300 is specified using three points P0, P1, P2 corresponding to its three corners. For example, triangle T1 is specified using points P0 1301, P1 1302, and P2 1303 such that T1={P0, P1, P2}={[X0, Y0, Z0], [X1, Y1, Z1], [X2, Y2, Z2]}. The triangles in the original polygonal mesh may be created using any number of well-known methods for converting point position data into a polygonal mesh that approximates the surface of an object.

Figure 4D:
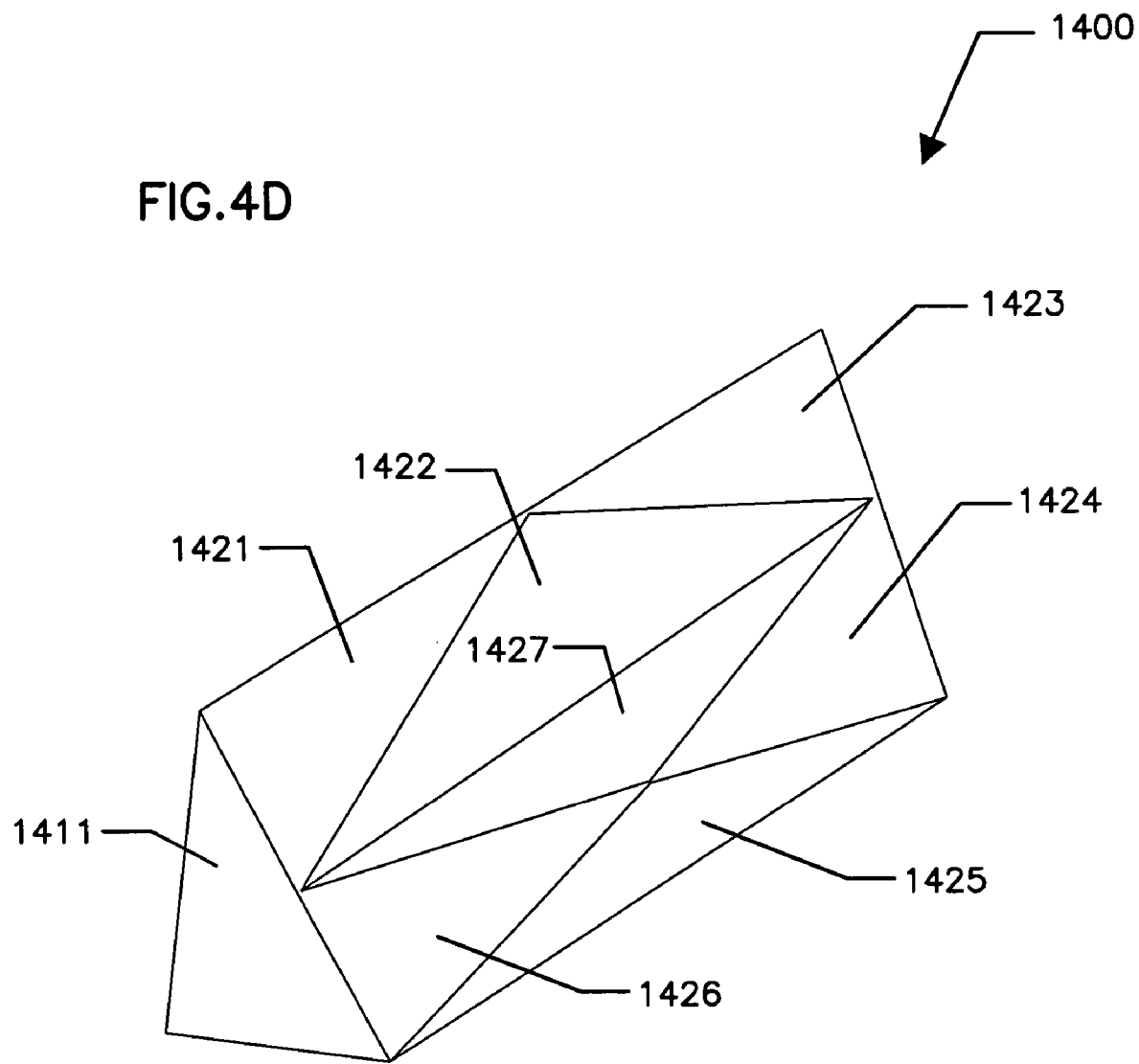

In FIG. 4D, a reduced polygonal mesh 1400 is generated by combining adjacent triangles in the original polygonal mesh 1300 when two or more triangles are sufficiently coplanar that they may be represented using a single triangle. For example, triangles 1311-1316 in FIG. 4C are reduced to triangle 1411 in FIG. 4D. Triangles 1421-1427 are also shown. The processing associated with this filtering operation controls the amount of triangle combination by setting a threshold relating to the minimum amount of deviation from a single plane for two or more triangles that is permitted before the two or more triangles are required to remain separate. This filtering process may be accomplished using a number of commercially available polygonal mesh processing products.

Figure 5:
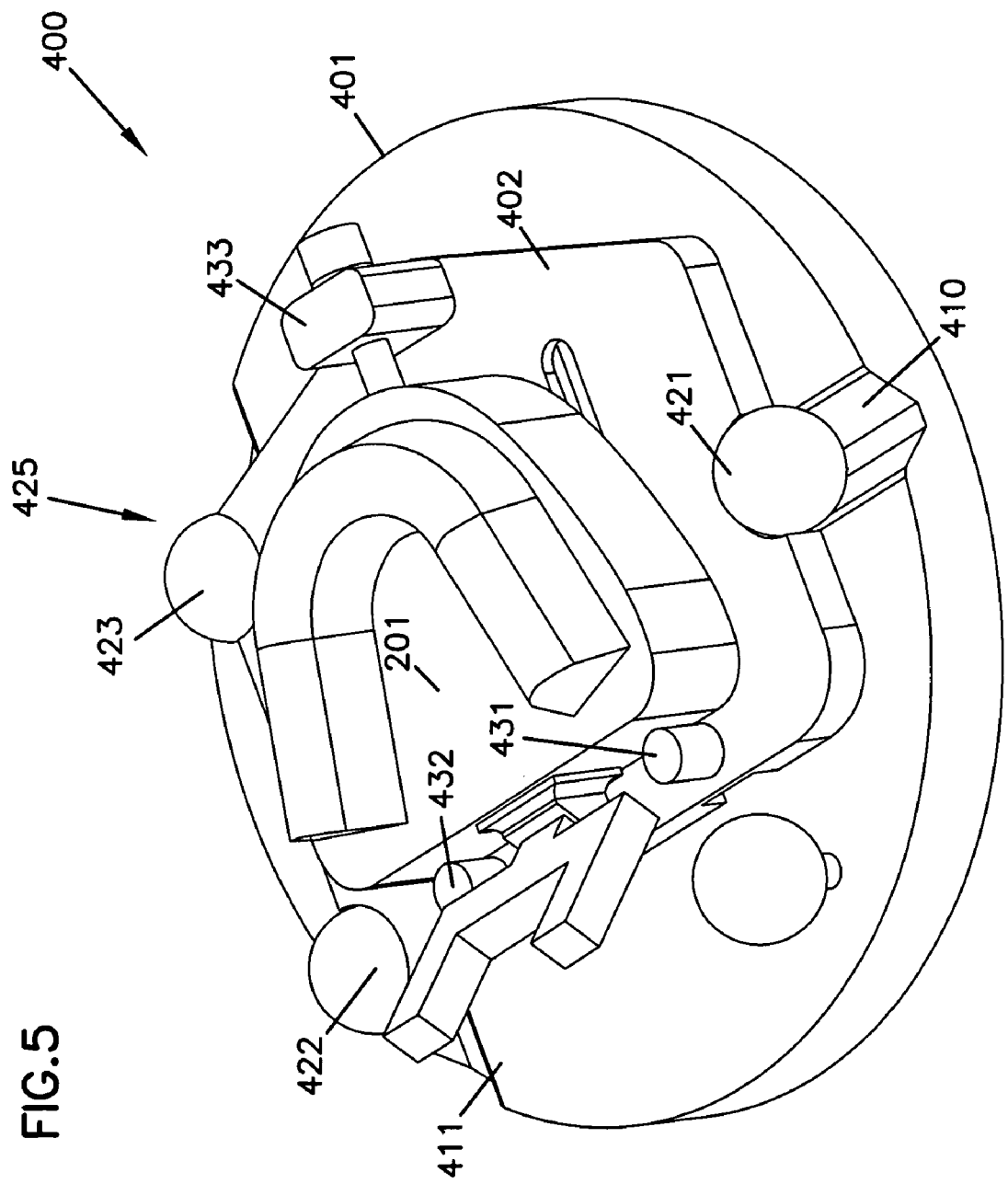
FIG. 5 illustrates one embodiment of a scanning assembly including a tooling plate structure mounted to a base plate structure.
Figure 6:
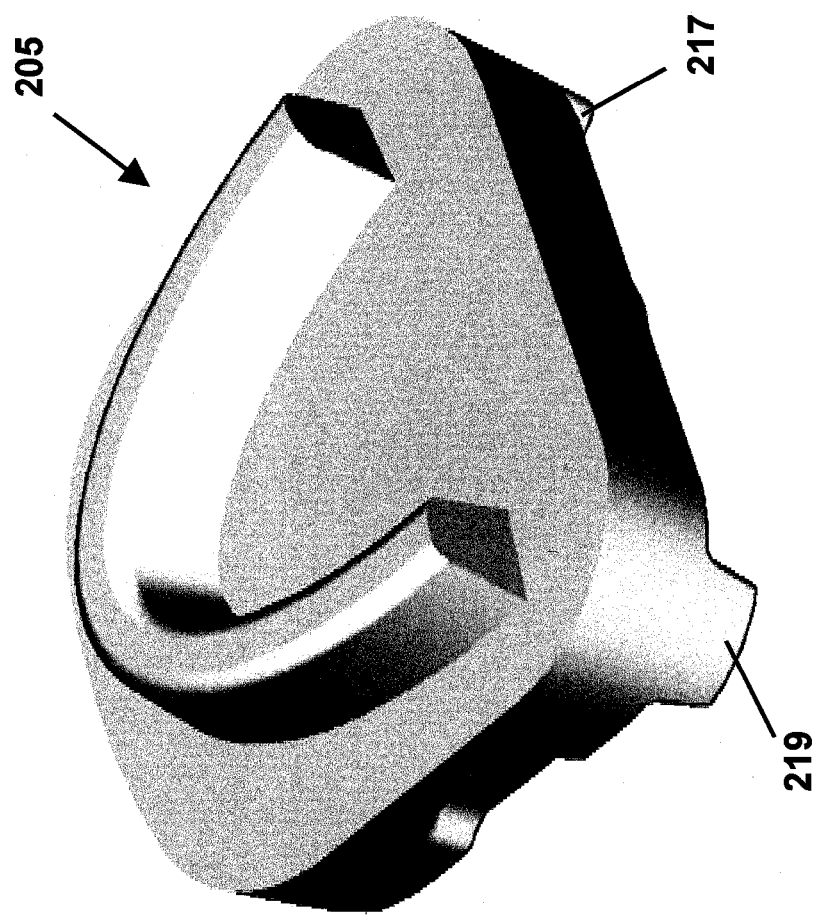
FIG. 6 illustrates a first side of a physical model configured to not require a tooling plate structure.
Figure 7:
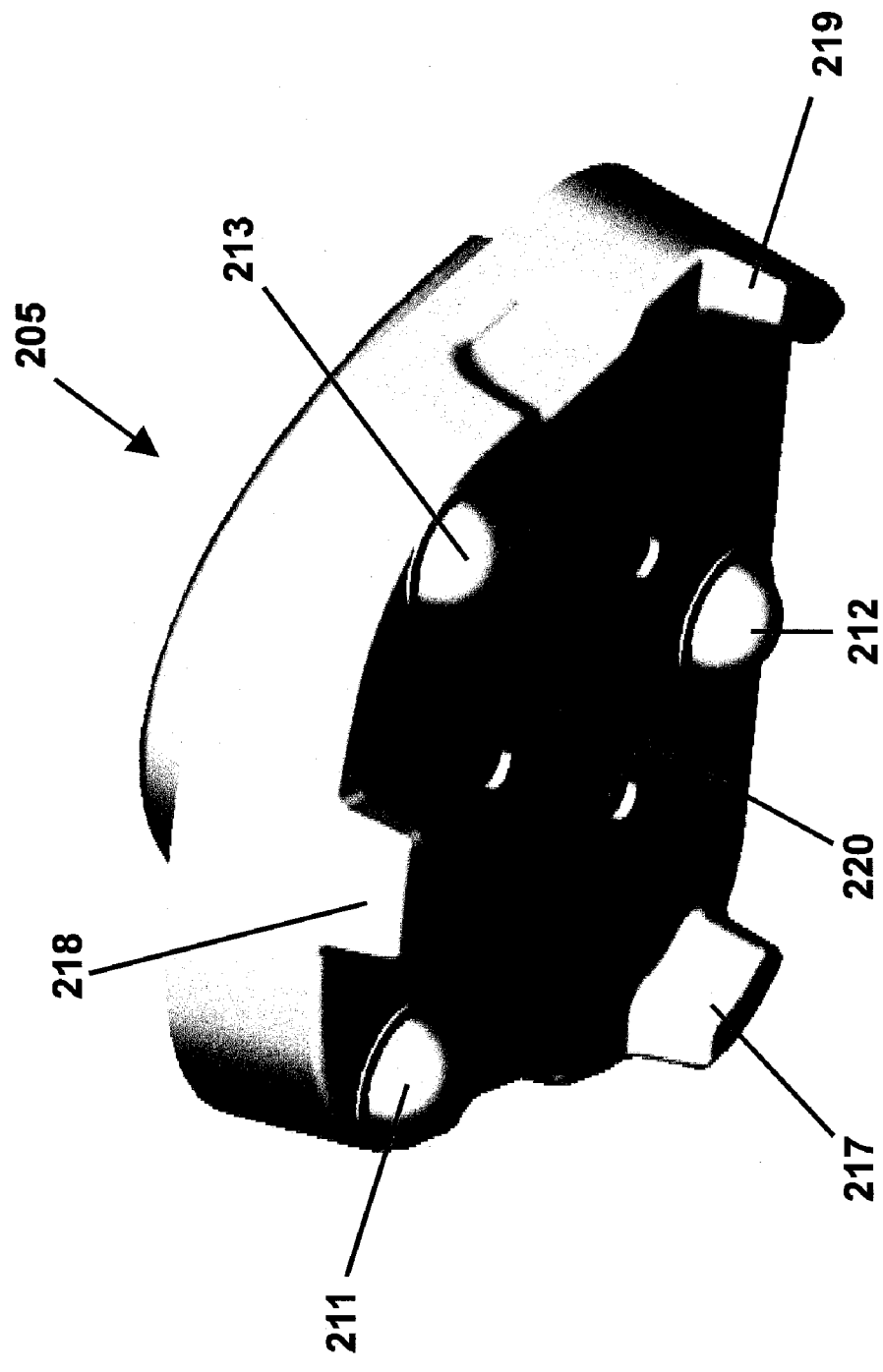
FIG. 7 illustrates an opposite side of the physical model shown in FIG. 6.

Referring now to FIGS. 5-7, an example configuration of scanning tools used in scanning physical models and converting them to electronic models will be described. FIG. 5 illustrates one embodiment of a scanning assembly 400 including a tooling plate structure 402 mounted to a base plate structure 401. The tooling plate structure 402 includes a set of reference points or markers 425. These reference points 425 may be arranged and configured according to any suitable distribution over the tooling plate structure 402. The assembly 400 further includes a physical model 201 of a dental impression mounted to the tooling plate 402. The physical model 201 is created from at least one dental impression taken of the patient.

One embodiment of the base plate structure 401 includes a plurality of alignment recesses for securing the tooling plate structure 402 to the base plate 401. In the example illustrated in FIG. 5, the plurality of alignment recesses include an x-axis alignment channel 411 and a y-axis alignment channel 410. These two alignment channels 410, 411 are perpendicular and co-planar within the plane defined by the top surface of the base plate structure 401. These two alignment channels 410, 411 are generally v-shaped such that the vertex of the channel defines the deepest point within the channel. In one embodiment, the plurality of reference points 425 includes a y-axis channel alignment sphere 421, a first x-axis channel alignment sphere 422, and a second x-axis channel alignment sphere 423. These three spheres 421, 422, 423 are defined by a radius corresponding to the size of the two alignment channels 410, 411 within the scanning base plate structure 401.

FIGS. 6-7 depict a partial, alternative embodiment of the assembly 400. FIG. 6 illustrates a first side of a physical model 205 configured to not require a tooling plate structure 402. FIG. 7 illustrates an opposite side of the physical model 205 shown in FIG. 6. Unlike the physical models 201, 202, the physical model 205 includes a plurality of directional protrusions 225 positioned along the side illustrated in FIG. 7. These directional protrusions 225 mate with the two alignment channels 410, 411 in much the same way as alignment spheres 421-423. According to one embodiment, these directional protrusions 225 include three directional hemispheres 211-213. Forming the directional hemispheres 211-213 directly onto the physical model 205 enables the physical model 205 to be easily replaced upon the scanning device or base plate structure 401 for scanning after being removed without having to realign the physical model 205 to a tooling plate structure 402.

In particular, to position the physical model 205 at a known and repeatable position relative to the scanning base plate structure 401, these spheres 211, 212, 213 are positioned to engage the two alignment channels 410, 411. This aligned position occurs because the first x-axis channel alignment sphere 212 and the second x-axis channel alignment sphere 213 position the physical model 205 at a known position relative to the scanning base plate structure 401 in the x-axis dimension. Similarly, the y-axis channel alignment sphere 211 engage the y-axis alignment channel 410 to position the physical model 205 at a known position relative to the scanning base plate structure 401 in the y-axis dimension. The combination of the two alignment channels 410, 411 and the three alignment spheres 211-213 enables the physical model 205 to be located at a single, repeatable position.

Another possible embodiment of the physical model 205 further includes a plurality of protruding members, which extend passed the hemispheres 211, 212, 213. In the example illustrated in FIG. 7, the plurality of protruding members includes three protruding members 217, 218, 219. The physical model 205 rests on these members 217, 218, 219 so that the hemispheres 211, 212, 213 do not become worn down. Yet another possible embodiment of the physical model 205 includes a metal washer 220 that enables the physical model 205 to be magnetically mounted to a scanning device, thereby better securing the physical model 205.

Figure 8:
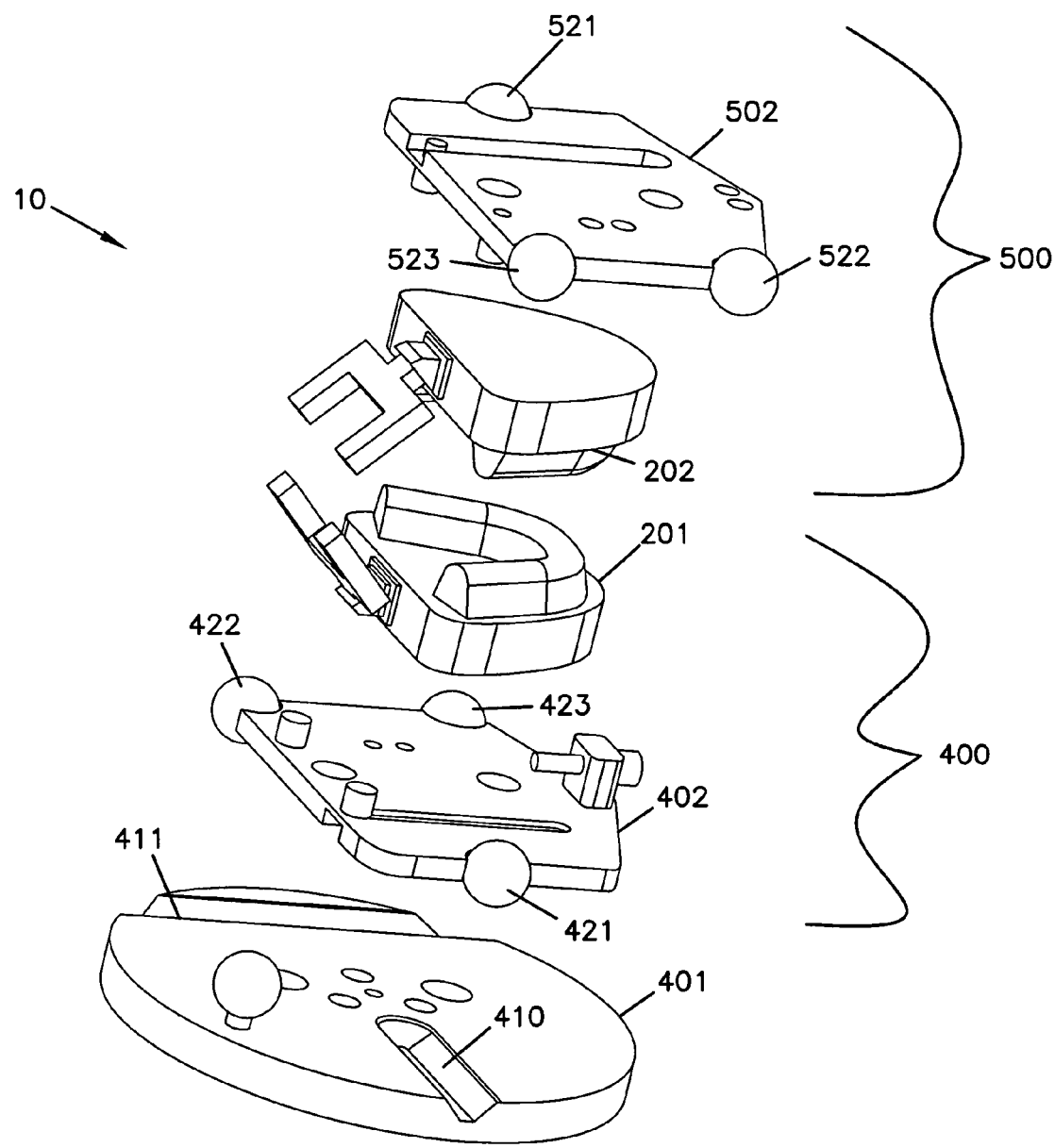
FIG. 8 illustrates an exploded view of an example scanning assembly.

Referring now to FIG. 8, an exploded view of an example scanning assembly 10 is illustrated. The first assembly 400 and a second assembly 500, which includes a physical model 202 representing the maxilla of the patient, are mounted to the scanning base plate structure 401. In one embodiment, the first assembly 400 includes the tooling plate structure 402 having three alignment spheres 421-423 and the physical model 201 corresponding to the mandible of the patient. The second assembly 500 includes a physical model 202 corresponding to the maxilla of the patient and another tooling plate structure 502 including three alignment spheres 521-523. In an alternative embodiment, physical models similar to physical model 205 described in FIGS. 6-7 are used, in which case the tooling plate structures 402, 502 are not used.

Figure 9:
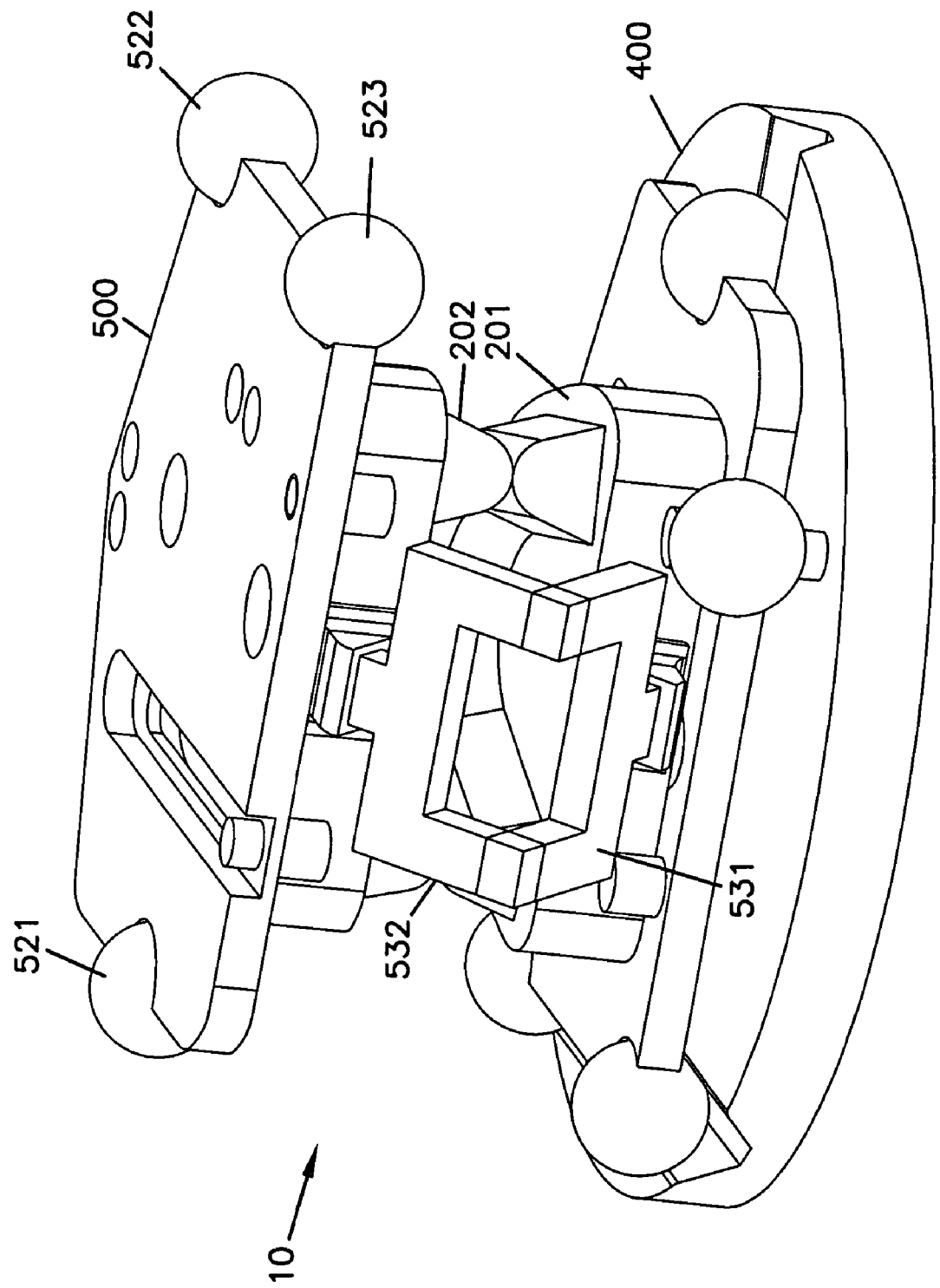
FIG. 9 illustrates a perspective view of one example embodiment of a scanning assembly including a first and second assembly.
Figure 10A:
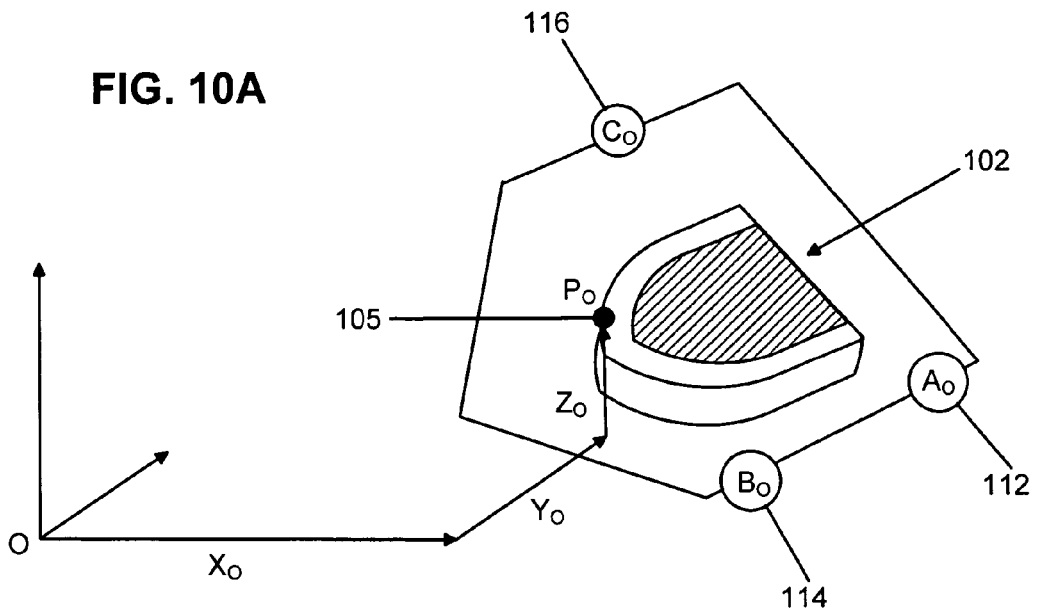
FIG. 10a illustrates a schematic of the electronic model representing the maxilla defined within the coordinate system O.
Figure 10B:
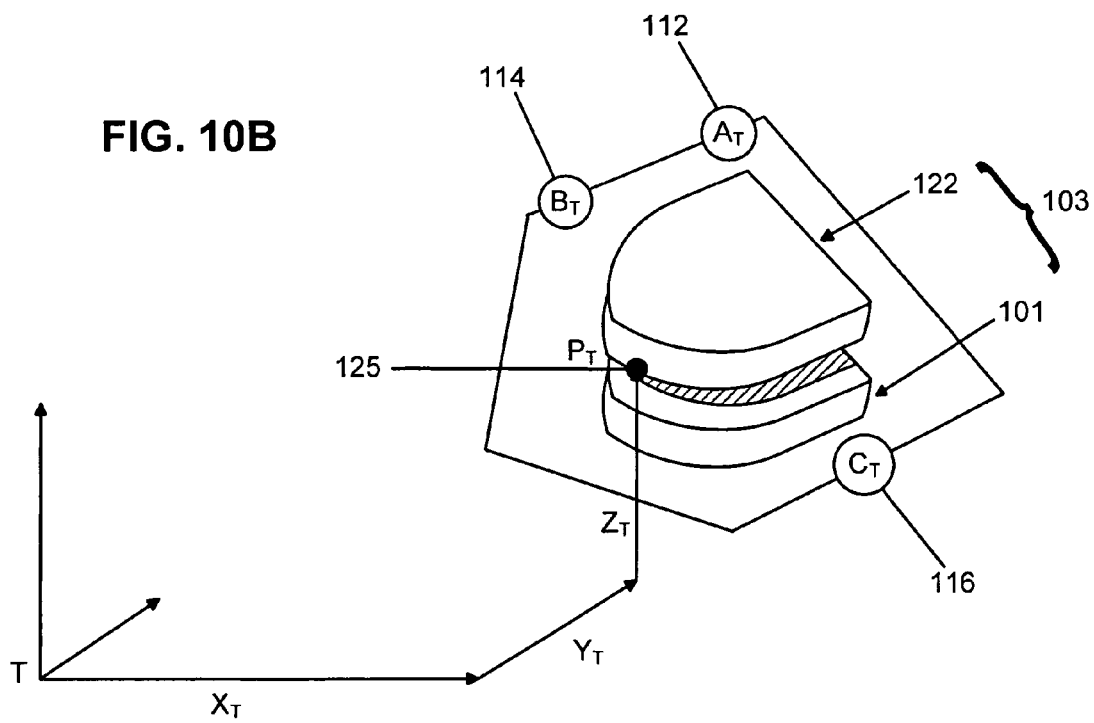
FIG. 10b illustrates the transformed electronic model representing the maxilla displayed with the electronic model representing the mandible within the coordinate system T.
Figure 11:
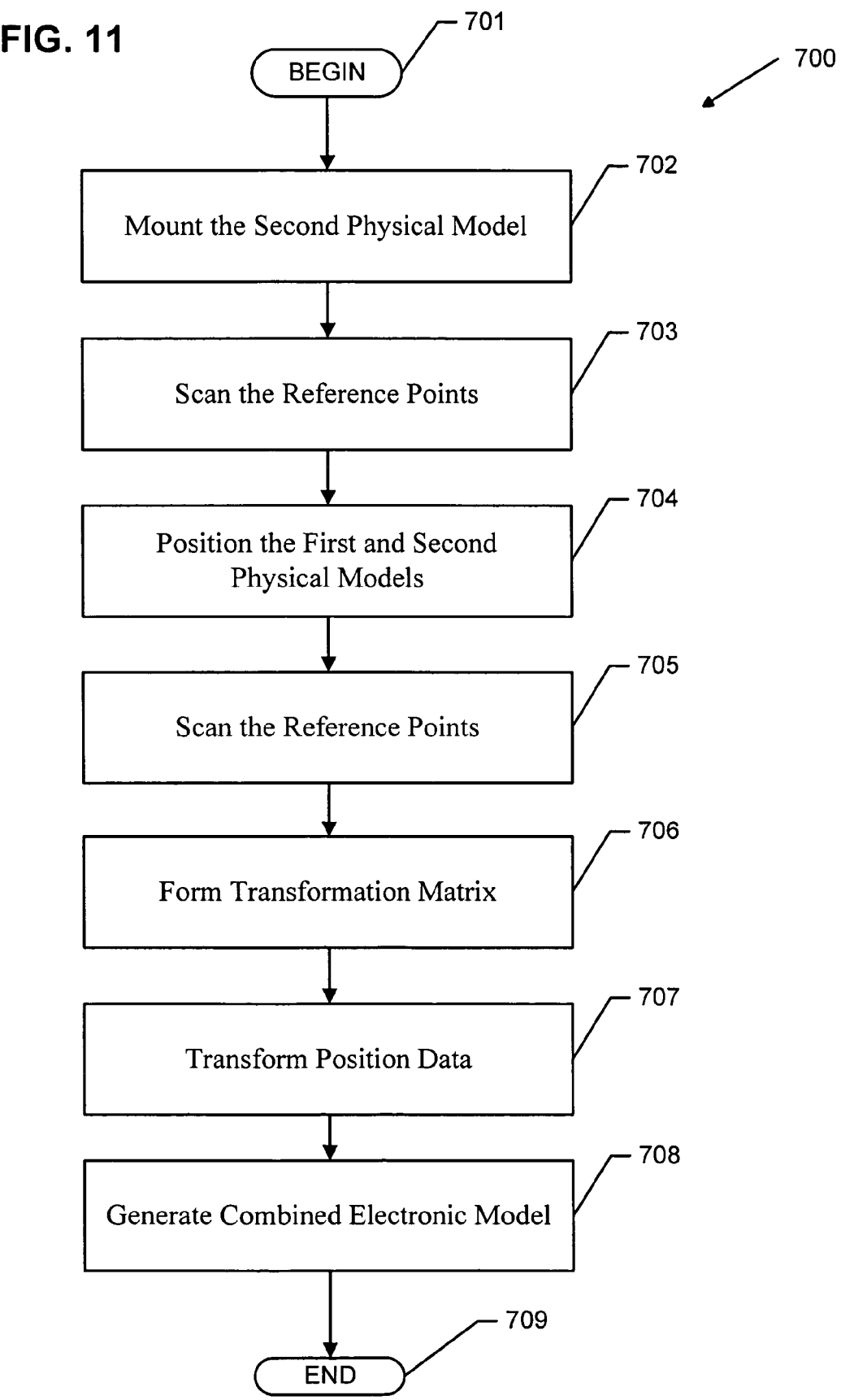
FIG. 11 illustrates a flow chart depicting the steps used to transform the point $P_O$ on the electronic model to the point $P_T$ on the transformed electronic model.

Referring now to FIG. 9-11, a combined electronic model 103 representing the maxilla and mandible of a patient within a common coordinate system is generated from the two assemblies 400, 500. FIG. 9 illustrates a perspective view of one example embodiment of a scanning assembly 10 including the first and second assembly 400, 500. Each assembly 400, 500 also includes an articulation member 531, 532. These two articulation members are coupled together to position the second assembly 500 at a position relative to the first assembly 400 to simulate the interaction of the maxilla and the mandible of a patient. By manipulating the arrangements of the two articulation members 531, 532, the two physical models 201, 202 may be positioned into any desired position relative to each other.

According to one embodiment, the desired position is defined by a user who moves the two assemblies 400, 500 until the two physical models 201, 202 are in a specific position relative to each other. In another embodiment, the physical models 201, 202 may be positioned according to a bite position record. Common examples of bite positions recorded by dental specialists include centric occlusion, centric relation, a protrusion bite, and a lateral excursion bite. One possible embodiment of such a bite record includes a bite wax impression obtained from the patient. The bite wax is created by having the patient bite down on a strip of wax, thereby leaving an impression showing the placement of the patient's teeth. The bite wax can then be placed in between the two physical models 201, 202 to allow proper alignment of the models. Another possible embodiment of such a bite record includes a medical image showing the patient's jaws or teeth.

Still referring to FIG. 9, each of the assemblies 400, 500 is scanned separately from the combined assembly 10. Separate electronic models 101, 102 are generated from these two assemblies 400, 500, each model 101, 102 being defined within a separate coordinate system T, O, respectively. To generate the combined electronic model 103, the two assemblies 400, 500 are arranged into a desired position and the combined assembly 10 is scanned. In one embodiment, when the combined assembly 10 is scanned, only the locations of the alignment spheres 521-523 on the second assembly 500 are determined. From this information, the location of any point on the second electronic model 102 may be transformed to a point on the coordinate system T used to define the first electronic model 101.

In one embodiment, the combined assembly 10 is typically scanned before either of the assemblies 400, 500 is individually scanned. In another embodiment, the combined assembly 10 is scanned after the first assembly 400 including the first physical model 201 is individually scanned. The first assembly 400 occupies the same position on the scanner while being scanned individually and while combined with the second assembly 500. Therefore, the combined assembly 10 will be scanned within the same coordinate system T as the first assembly 400. The position points of the second assembly 500 are converted from the coordinate system O into position points in the coordinate system T in order to place all of the points used to define the two electronic models 101, 102 within a single coordinate system.

Referring now to FIGS. 10A and 10B, the position of the second electronic model 102 is determined within the same coordinate system T as the first electronic model 101. FIG. 10A illustrates a schematic of the second electronic model 102, which corresponds with physical model 202 of a maxilla, defined within the coordinate system O. In the illustrated embodiment, the electronic model 102 is displayed dentition side up because that is how the corresponding physical model 202 is scanned in order to obtain positional data on the dentition. The initial electronic model 102 has a point $P_O$ 105 located within coordinate system O, such that $P_O=\{X_O, Y_O, Z_O\}$. The relative positions of electronic reference points 112, 114, 116 at positions $A_O$, $B_O$, and $C_O$, respectively are also depicted. In one embodiment, the reference points 112, 114, 116 refer to the positions of the reference points 525 on the tooling plate 502 (see FIG. 5). In another embodiment, the reference points 112, 114, 116 represent the three protruding reference points 211-213 (e.g., or hemispheres) on the physical model 205 (see FIG. 7).

Referring now to FIG. 10B, the electronic model 102 is transformed into an electronic model 122 defined within the coordinate system T. FIG. 10B illustrates the transformed electronic model 122 displayed with the electronic model 101. The transformed electronic model 122 is now right side up and occupies a position over the electronic model 101 of the mandible. A point $P_T$ 125 on the transformed electronic model 122 corresponds to the point $P_O$ 105 on the electronic model 102. The point $P_T$ is located within the coordinate system T such that $P_T=\{X_T, Y_T, Z_T\}$. Reference points 112, 114, and 116 have also been transformed to occupy positions $A_T$, $B_T$, and $C_T$, respectively. Electronic model 101 and transformed electronic model 122 form the combined electronic model 103.

FIG. 11 illustrates a flow chart 700 depicting the steps used to transform the point $P_O$ 105 on the electronic model 102 to the point $P_T$ 125 on the transformed electronic model 122. These steps will be described herein with reference to FIGS. 9, 10a and 10b. The process assumes that the first physical model 201 has already been scanned and that the corresponding electronic model 101 has already been generated. The process begins at module 701 and proceeds to mounting operation 702 in which the second physical model 202 is mounted dentition side up on the scanning device (not shown). Next, scanning operation 703 includes scanning the dentition portion of the physical model 202 and the reference points 225 on the second physical model 202 to obtain positional data. In one embodiment, this positional data is stored in memory as a point cloud data file. In another embodiment, the positional data is used to generate an initial electronic model 102 of the maxilla.

The process proceeds to positioning operation 704 in which the first and second physical models 201, 202 are positioned on the scanner into a desired position. For example, in dental modeling, the first and second physical models 201, 202 are positioned so as to represent the relationship between the maxilla and mandible of a patient in various bite positions. In various embodiments, methods of positioning include bite records, medical images, and any other suitable method.

The reference points 225 are scanned in reference scanning operation 705. The positional data obtained from the scan corresponds to reference points 112, 114, and 116 on the transformed electronic model 122. According to one embodiment, the reference points 225 include the alignment spheres 521-523 on the tooling plate structure 502. According to another embodiment, the reference points 225 include the directional protrusions 211-213 on the physical model 205.

In matrix formation operation 706, a transformation matrix [M] is created using the positions of the reference points 112, 114, 116 on the initial electronic model 102 and the positions of the reference points 112, 114, 116 on the transformed electronic model 122. The transformation matrix [M] is created based on an algorithm known in the art for mapping at least three points from one position in three-dimensional space to another. In one embodiment, the transformation matrix [M] is a four-by-four matrix [M4]. As mentioned above with respect to FIGS. 10a and 10b, a point $P_O$ on the electronic model 102 can be defined as having a position $P=(X_O, Y_O, Z_O)$. In the example of a four-by-four matrix, by adding a fourth dimension to the point coordinate and assuming the fourth point to be equal to 1, so that $P_O=(X_O, Y_O, Z_O, 1)$, the point $P_O$ can be multiplied by the transformation matrix [M4] to yield the translated point $P_T=(X_T, Y_T, Z_T, 1)$.

The process then proceeds to transformation operation 707 in which each point of positional data scanned from the second physical model 202 is transformed by multiplying the point by the transformation matrix [M4]. Once the position data transformation operation 707 completes, operation 708 uses the transformed data points to generate a combined electronic model 103 representing the maxilla and mandible. This combined electronic model 103 enables a user to manipulate one model while keeping track of its locations relative to the other. The process ends at module 709.

Referring now to FIGS. 12-15, another possible embodiment of the invention enables a user to determine how the left and/or right condyle of a patient will be displaced during jaw articulation (i.e., or when the patient's mandible is moved relative to the maxilla). The displacement of each condyle point CR, CL is calculated using a transformation matrix [M] created from positional data obtained from scans of the reference points 225 on the second physical model 202 when arranged in two or more bite positions.

Figure 12:
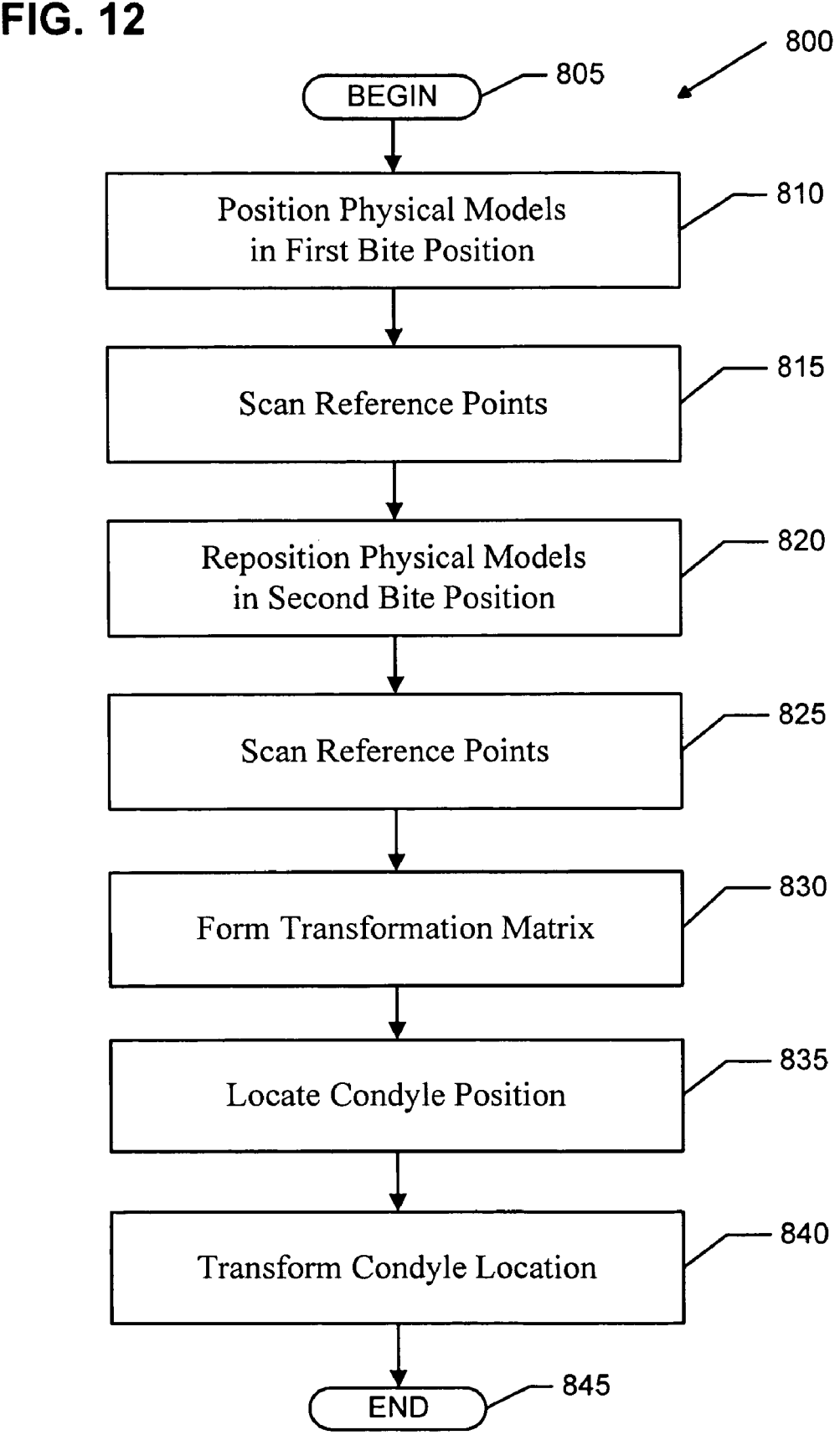
FIG. 12 illustrates an example operation flow for a process for generating a condyle transformation matrix $M_C$.

FIG. 12 illustrates an example operation flow for a process 800 for generating a condyle transformation matrix [$M_C$]. The process 800 uses the first and second physical models 201, 202 (or two alternative physical models 205) corresponding to the mandible and maxilla, a scanning device (not shown), and a scanning assembly 10 substantially as described above with respect to FIGS. 6, 7, 9, 10a, and 10b. The process assumes that electronic images 101, 122 of the physical models 201, 202 and the combined electronic model 103 have already been generated and converted to a common coordinate system. Alternatively, the electronic models 101, 122, 103 can all be generated after completing the process 800, or not at all.

The process 800 begins at module 805 and proceeds to positioning operation 810 in which a first and second physical model 201, 202 are positioned according to a first bite record using the techniques described above with reference to FIG. 9. This bite record can be thought of as "home base" so to speak for the electronic model 103. All transformed electronic model positions will be generated with reference to this first bite record position. Consequently, condyle displacement will be measured with respect to the first bite position.

First scanning operation 815 scans the position of each directional protrusion 225 on the second physical model 202 using the scanning device to create a first set of positional data. Next, in repositioning operation 820, the first and second physical models 201, 202 are repositioned according to a second bite record. In second scanning operation 825, the directional protrusions 225 again are scanned on the second physical model 202 to create a second set of positional data. According to one embodiment, operations 820 and 825 are repeated multiple times for a variety of bite records. For each successive bite record, a different transformation matrix [$M_C$] can be created to define jaw articulation between the bite record and the first bite record (i.e., home base).

Matrix formation operation 830 uses the data point corresponding to the center of each of the directional protrusions 225 taken from two of the bite scans to create the transformation matrix [$M_C$]. The first and second sets of positional data yield a four-by-four transformation matrix [$M_{C4}$]. The transformation matrix [$M_{C4}$] can be used to determine the displacement of any point on the second electronic model 122 when the physical model 202 is moved from the first bite position to the second bite position.

The process now proceeds to condyle locating operation 835, which includes determining the positions Pc=(Xc, Yc, Zc) of one or both of the patient's condyles within the common coordinate system T. This operation 835 is described in detail herein with respect to FIGS. 13-15. Transforming operation 840 transforms the position of the condyle Pc from a first bite position $Pc_1$ to a second bite position $Pc_2$ using the transformation matrix [$M_C$]. The process ends at module 845.

Using the transformation matrix, the user can view the electronic model 103 of the patient's mandible and maxilla in both the first bite position and the transformed bite position. Generally, when positioning the physical models 201, 202 on the combined assembly 10, the second model 202 is positioned while the first model 201 remains stationary. However, when a patient forms the different bite positions with her jaws, the mandible moves while the maxilla remains stationary. In order to seem more natural to the user, therefore, one embodiment displays the mandible of electronic model 103 (i.e., or electronic model 101) moving between bite positions while the maxilla (i.e., or electronic model 122) remains stationary.

The transformation matrix [$M_{C4}$] transforms the position of each of the points on the electronic model 101 within the coordinate system T to the position that point would occupy if the electronic model 101 were moved to the second bite position. According to another possible embodiment, the electronic model 122 of the maxilla would be shown moving. Furthermore, once the position of each point on the electronic model 103 is known for each bite position, it is possible to interpolate the positions each point would progress through when moving from the first bite position to any of the other bite positions. In one embodiment, the combined electronic model 103 is displayed moving through these points as well.

Figure 13:
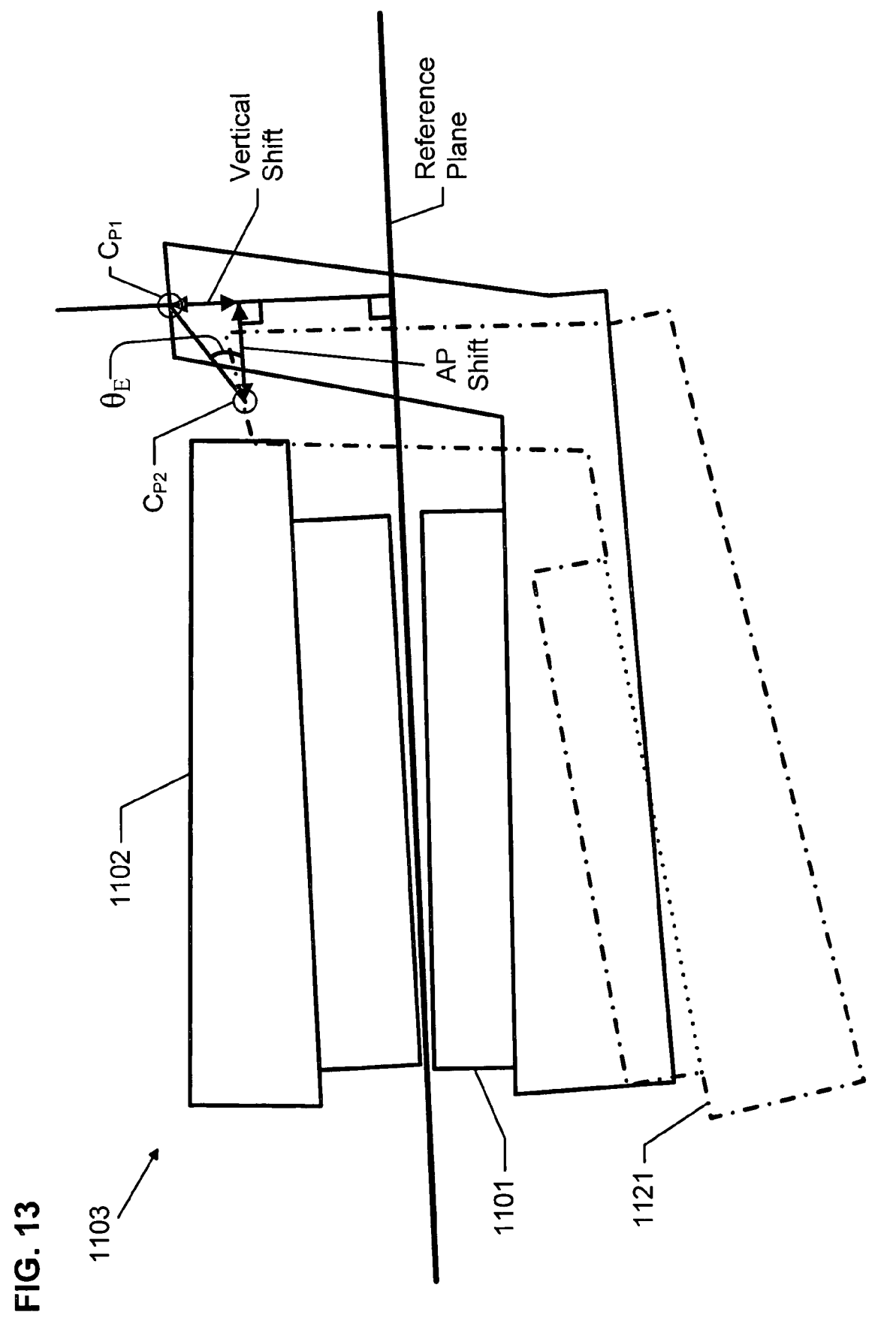
FIG. 13 illustrates an example method of measuring the vertical and AP shift of a condyle.
Figure 14:
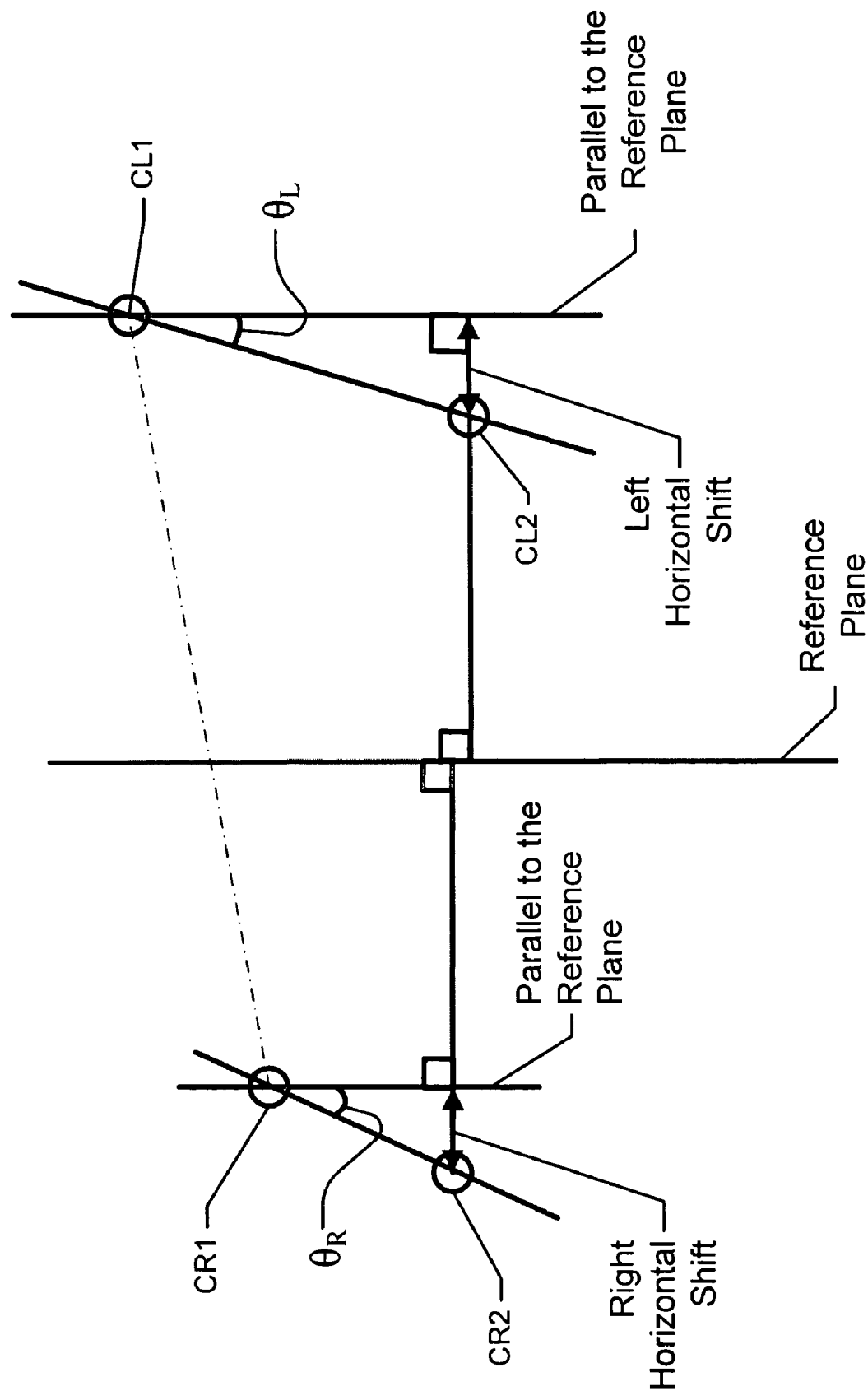
FIG. 14 illustrates an example method of measuring the horizontal shift in condyle position.

Referring now to FIGS. 13-14, determining condyle displacement includes determining over what distance and in what direction a patient's condyle shifts between bite positions. For example, the shift in condyle position can be described as displacement along three dimensions (e.g., an x-axis, a y-axis, and a z-axis). The axes are defined relative to a reference plane. In various embodiments, reference planes include an occlusal plane, a Frankfort Horizontal plane, a coronal plane, a sagittal plane, and any other such suitable plane. In one embodiment, the three measurements taken to calculate condyle displacement are the vertical shift, the anterior-posterior (AP) shift, and the horizontal shift.

An example method of measuring the vertical and AP shift of a condyle is illustrated in FIG. 13. A combined electronic model 1103 including an electronic model 1101 of a mandible and an electronic model 1102 of a maxilla is positioned in a first bite position. A reference plane is also shown extending between the maxilla and mandible. An electronic model 1121 representing the mandible in a second bite position is also shown in dashed lines. The position of the condyle $C_{P1}$, $C_{P2}$ on each electronic model 1101, 1121, respectively, is indicated.

According to one embodiment, measuring the vertical shift between the condyle positions $C_{P1}$, $C_{P2}$, includes drawing a first line through the first condyle position $C_{P1}$ such that the first line is perpendicular to the reference plane. A second line is drawn through the second condyle position $C_{P2}$ such that the second line is perpendicular to the first line (i.e., parallel with the reference plane). The vertical shift of the condyle refers to the distance between the first condyle position $C_{P1}$ and the point of intersection of the first and second lines. The AP shift refers to the distance between the second condyle position $C_{P2}$ and the point of intersection of the first and second lines. In some embodiments, a condylar angle $\theta_E$ between the second line and a line connecting the two condyle position points $C_{P1}$, $C_{P2}$ is also of interest.

An example method of measuring the horizontal shift in condyle position is illustrated in FIG. 14. Schematic representations of a patient's right condyle CR1, CR2 and left condyle CL1, CL2 in a first and second bite position, respectively, are illustrated in FIG. 14. A reference plane is also shown. In one embodiment, the reference plane is the sagittal plane of the patient. In another embodiment, the reference plane is the midline plane of the patient. However, other such reference planes can be used.

In one embodiment, determining the horizontal shift of the right condyle includes drawing a first line through the right condyle in one of the bite positions (e.g., CR2) such that the line is perpendicular to the reference plane. A second, orthogonal line is drawn through the other right condyle (e.g., CR1) such that the second line intersects the first line at a right angle. The horizontal shift of the condyle refers to the distance between the point of intersection of the first and second line and the position of the right condyle CR2 through which the first line passes. The horizontal shift for the left condyle is determined in substantially the same fashion. In some embodiments, the user is also interested in the Bennett angle $\theta_R$, $\theta_L$ for each condyle. The Bennett angle is the angle between the reference plane and a third line connecting the condyle position points for the two bite positions.

Figure 15:
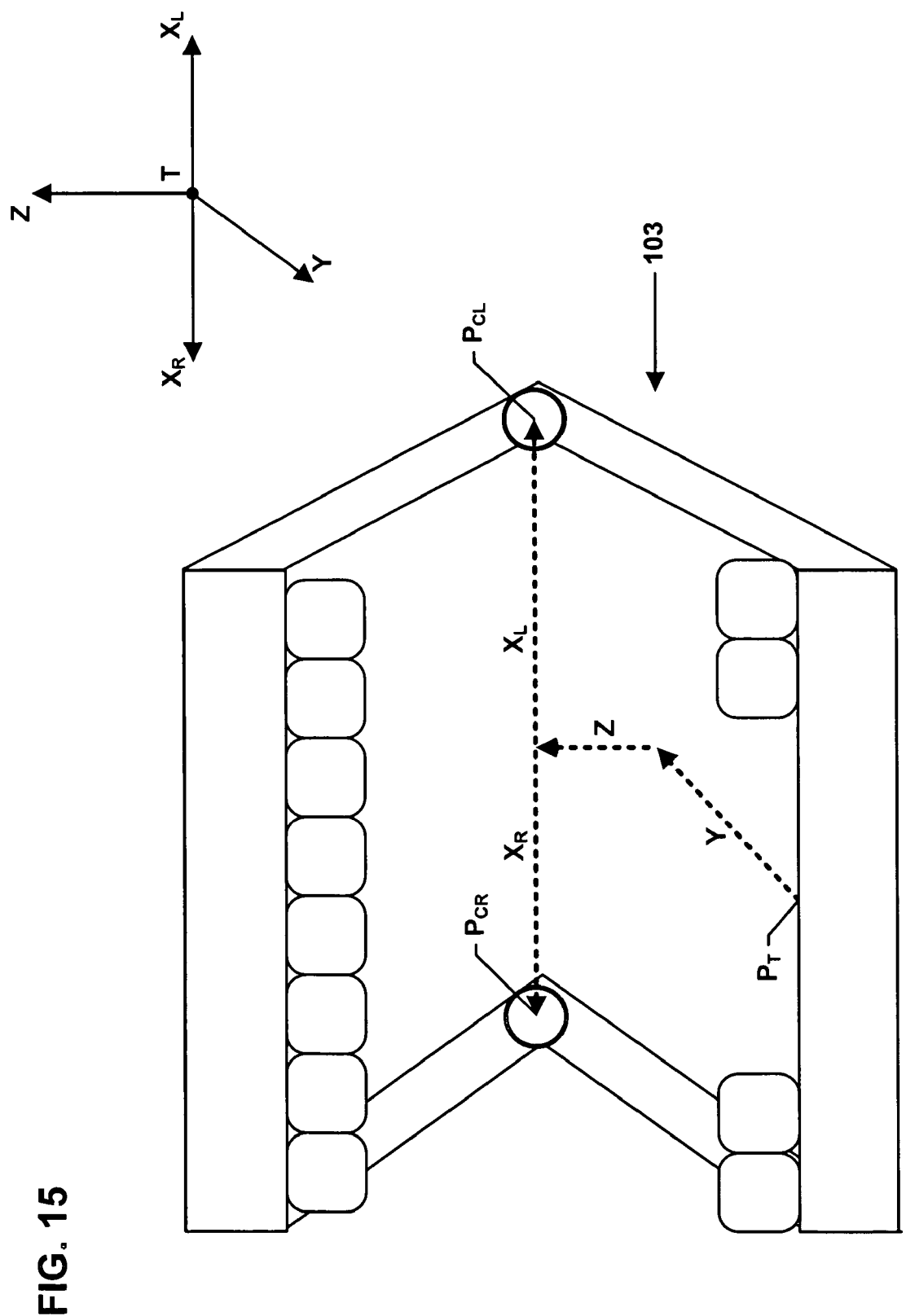
FIG. 15 illustrates one example method of determining the location of the patient's condyle.

Referring now to FIG. 15, determining displacement of the patient's condyle includes locating the condyle in relation to a point on the scanned positional data forming one of the electronic models 101, 122, 103. FIG. 15 illustrates one example method of determining the location of the patient's condyle including measuring the distance along an x-axis, a y-axis, and a z-axis of a coordinate system T between a patient's condyle Pc and a known point position $P_T$ on the patient's mandible. In varying embodiments, the point Pc can refer to either the patient's left condyle $P_{CL}$ or the patient's right condyle $P_{CR}$. In one embodiment, the point $P_T$ corresponds to a selected point on the electronic model 103. Because the point $P_T$ is known within the coordinate system T, the position of the condyle Pc in another bite position can be determined by using the transformation matrix $[M_C]$ described above in FIGS. 10(a-b) and 11. Also, as discussed above, it is possible to interpolate the positions Pc through which the condyle would progress when moving from one bite position to the another.

Figure 16:
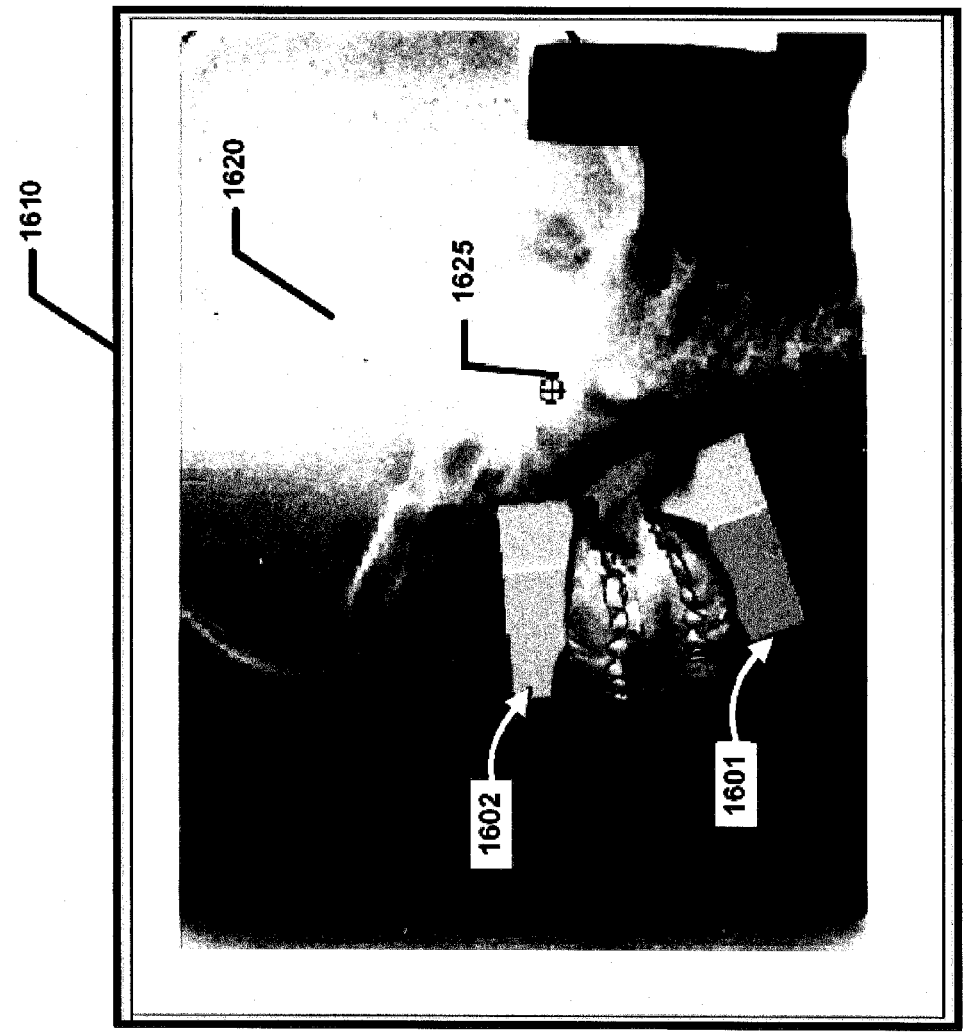
FIG. 16 illustrates using a digital copy of an X-ray to visually determine the y-axis and z-axis values for the position of the condyle.

Referring to FIG. 16, in one embodiment, an electronic copy of a physiological image is used to determine a position of the condyle Pc along at least a first and second axis in relation to other physiological structures of the patient. Examples of medical images include a Cephalometric tracing, a photograph, an X-ray, or any other similar image. For example, FIG. 16 illustrates using a digital copy of an X-ray 1610 to visually determine the y-axis and z-axis values for the position Pc of the condyle.

Electronic models 1601, 1602 (i.e., or a combined electronic model 1103) representing the mandible and the maxilla are superimposed upon the digital copy of the X-ray 1610 of the patient's skull 1620. The X-ray 1610 is rotated and/or shifted relative to the electronic models 1601, 1602 so that the X-ray 1610 is oriented similarly to the electronic models 1601, 1602. The X-ray 1610 is then resized so that the sizes of the patient's mandible and maxilla in the X-ray 1610 correspond to the sizes of the electronic models 1601, 1602. Positioning, orienting, and sizing the X-Ray 1610 as such substantially places the points on the X-ray 1610 in the same coordinate system T as the electronic models 1601, 1602. A point 1625 on the X-ray 1610 is then selected to define the y-axis position Pcy and z-axis position Pcz of the patient's condyle on the X-ray 1610.

In one embodiment, a user inputs the x-axis position Pcx of each condyle based on physical measurements. In another embodiment, a second physiological image taken at a different orientation (e.g., an occlusal view) can be used to obtain the x-axis position Pcx value substantially as described herein. According to another possible embodiment, the x-axis, y-axis, and/or z-axis positions Pcx, Pcy, Pcz of each condyle are determined by using a face bow or other physical measuring device. In another embodiment, the selection of the point 1625 or the x-axis position Pcx is based on a visual determination made by the user. In yet another embodiment, computer software calculates the condyle's position 1625.

Figure 17:
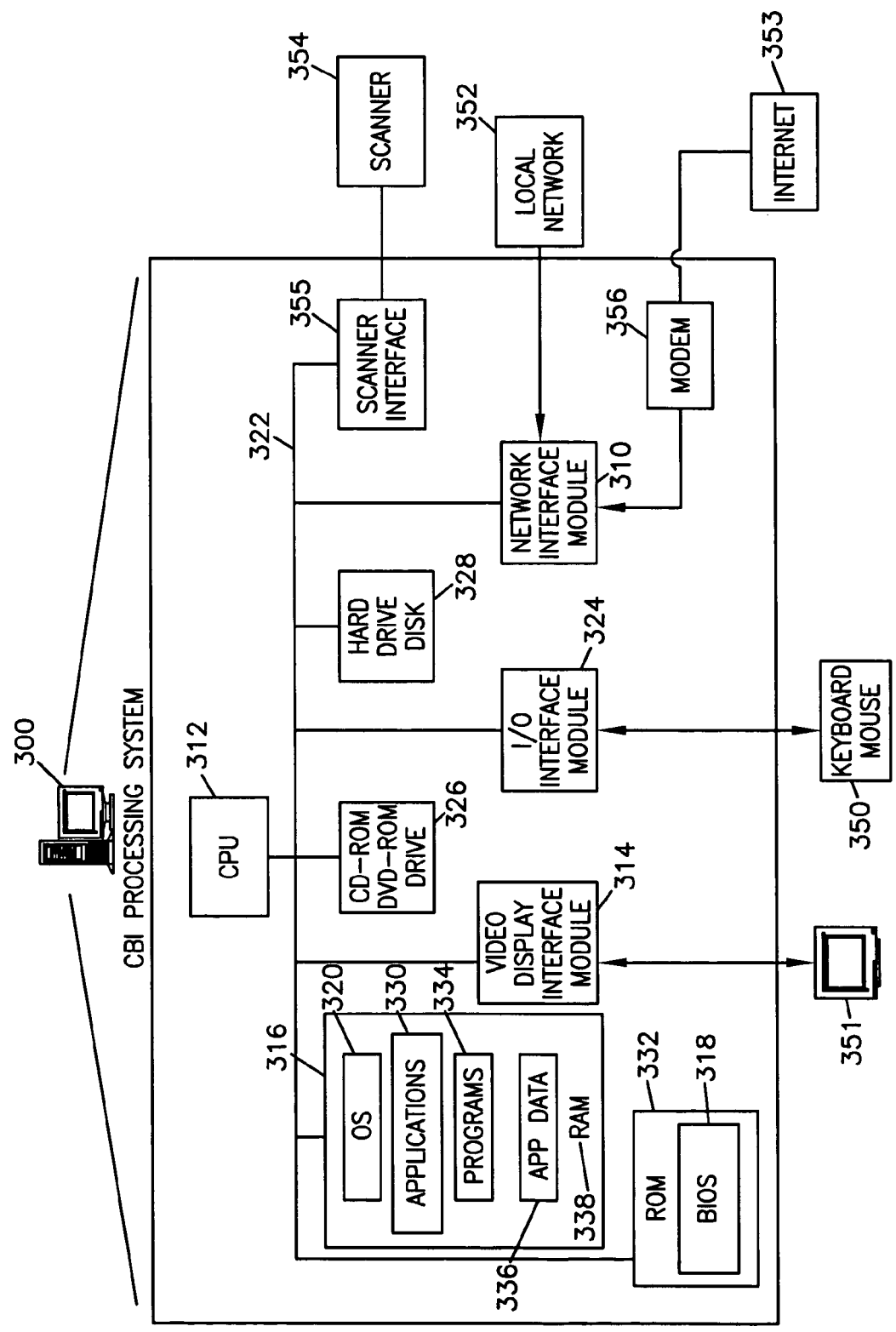
FIG. 17 illustrates one possible embodiment of a computing system for generating, manipulating, and storing the various electronic models and/or positional data.

FIG. 17 illustrates one possible embodiment of a computing system for generating, manipulating, and storing the various electronic models and/or positional data. The processing system 300 is operative to provide a dental scanning coordinate processing system. Those of ordinary skill in the art will appreciate that the dental scanning coordinate processing system 300 may include many more components than those shown in FIG. 17. However, the components shown are sufficient to disclose an illustrative embodiment for practicing embodiments disclosed herein. For example, those of ordinary skill in the art will appreciate that a network interface unit 310 includes the necessary circuitry for coupling the dental scanning coordinate system processing system 300 to a network of other computing systems 352, 353, and is constructed for use with various communication protocols including the TCP/IP protocol. In some embodiments, the network interface unit 310 is a card contained within neural network training and data collection system.

The dental scanning coordinate system processing system 300 also includes processing unit 312, video display adapter 314, and a mass memory 316, all coupled via bus 322. The mass memory generally includes RAM 338, ROM 332, and one or more permanent mass storage devices, such as hard disk drive 328, a tape drive, CD-ROM/DVD-ROM drive 326, and/or a floppy disk drive (not shown). The mass memory stores an operating system 320 for controlling the operation of the dental scanning coordinate processing system 300. It will be appreciated that this component may include a general purpose server operating system as is known to those of ordinary skill in the art, such as UNIX, MAC OS™, LINUX™, OR Microsoft WINDOWS NT®. Basic input/output system ("BIOS") 318 is also provided for controlling the low-level operation of processing system 300.

The mass memory as described above includes another type of computer-readable media, namely computer storage media. Computer storage media may include volatile and nonvolatile, removable and non-removable media implemented in any method or technology for storage of information, such as computer readable instructions, data structures, program modules or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

In some embodiments, the mass memory also stores program code and data for providing a software development and neural network analysis and training system. More specifically, the mass memory stores applications including common coordinate system application program 330, programs 334, and similar data processing applications 336. The common coordinate system application program 330 includes computer executable instructions which, when executed by the computer system 300, perform the logic desired herein.

Dental scanning coordinate system processing system 300 also includes input/output interface 324, Video/Display interface 314, and scanning interface 355 for communicating with external devices, such as a mouse or keyboard 350, scanner 354, display screen 351, or other input devices not shown in FIG. 17. Likewise, other embodiments of a dental scanning coordinate system processing system 300 further include additional mass storage facilities such as CD-ROM/DVD-ROM drive 326 and hard disk drive 328. In one embodiment, the hard disk drive 328 is utilized by the dental scanning coordinate system processing system 300 to store, among other things, application programs, databases, and program data used by the common coordinate system application program 330.

The operation environment illustrated in FIG. 17 is only one example of a suitable operating environment and is not intended to suggest any limitations to the scope of use or functionality of the invention. Other well known computing systems, environments, and/or configurations that may be suitable for use with the invention include, but are not limited to, personal computers, server computers, held-held or laptop devices, multiprocessor systems, microprocessor-based systems, programmable consumer electronics, network PCs, minicomputers, mainframe computers, distributed computing environments that include any of the above systems or devices, and the like.

The invention may also be described in the general context of computer-executable instructions, such as program modules, executed by one or more computers or other devices. Generally, program modules include routines, programs, objects, components, data structures, etc. that perform particular tasks or implement particular abstract data types. Typically the functionality of the program modules may be combined or distributed in desired various embodiments.

A processing device attached to a communications network typically includes at least some form of computer readable media. Computer readable media can be any available media that can be accessed by these devices. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by process devices.

Communication media typically embodies computer readable instructions, data structure, program modules or other data in a modulated data signal such as a carrier wave or other transport mechanism and includes any information delivery media. The term "modulated data signal" means a signal that has one or more of its characteristics set or changed in such a manner as to encode information in a signal. By way of example, and not limitation, communication media includes wired media such as a wired network or direct-wired connection, and wireless media such as an acoustic, RF, infrared and other wireless media. Combinations of any of the above should also be included within the scope of computer readable media.

Additionally, the embodiments described herein can be implemented as a logical operation performed by a programmable processing device. The logical operation of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

While the above embodiments of the present invention describe a system, method and article of manufacture for generating an electronic model for a dental impression having a common coordinate system, one skilled in the art will recognize that the use of a particular computing architecture for a data processing system are merely example embodiments of the present invention. It is to be understood that other embodiments may be utilized and operation changes may be made without departing from the scope of the present invention as recited in the attached claims.

As such, the foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto.

I claim:

1. A method for determining condyle displacement for a patient, the method comprising:
   mounting a first physical model onto a first scanning plate module to form a first mounting arrangement, the first physical model being representative of a first set of teeth of the patient;
   mounting a second physical model onto a second scanning plate module to form a second mounting arrangement, the second physical model being representative of a second set of teeth of the patient;
   positioning the first and second mounting arrangements on a base plate module to arrange the first physical model relative to the second physical model within a coordinate system of a scanning device according to a first bite record;
   scanning three or more reference sites on at least one of the mounting arrangements with the scanning device to obtain a first set of positional data;
   positioning the first and second mounting arrangements on the base plate module to arrange the first and second physical models within the coordinate system of the scanning device according to a second bite record;
   scanning the three or more reference sites with the scanning device to obtain a second set of positional data;
   determining a transformation matrix from the first and second sets of positional data with a data processing system;
   determining a first location of a point corresponding to a condyle of the patient in relation to the first set of positional data;
   determining with the data processing system a second location of the point corresponding to the condyle in relation to the second set of positional data based on the transformation matrix; and
   generating a manipulable electronic model based on the first and second sets of positional data and the transformation matrix to assess condyle displacement of the patient.

2. The method of claim 1, wherein determining the first location of the point corresponding to the condyle includes measuring a distance between the condyle of the patient and at least one point on one of the mandible and the maxilla of the patient using a face bow.

3. The method of claim 1, wherein determining the first location of the point corresponding to the condyle includes:
   displaying a medical record image showing at least one condyle of the patient;
   superimposing an electronic model corresponding to one of the mandible and the maxilla of the patient over the medical record image; and
   selecting a point on the medical record image, wherein the selected point corresponds to the position of the condyle.

4. The method of claim 3, wherein a computer software program selects the condyle point on the medical record image.

5. The method of claim 1, wherein positioning the first and second mounting arrangements on the base plate module further comprises:
mounting the first mounting arrangement to the base plate module of the scanning device, the base plate module positioning the first mounting arrangement at a known position within the coordinate system of the scanning device; and
mounting the second mounting arrangement to the first mounting arrangement on the base plate module of the scanning device.

6. The method of claim 5, wherein the first physical model represents teeth of a mandible of the patient and the second physical model represents teeth of a maxilla of the patient.

7. The method of claim 5, wherein mounting the second mounting arrangement to the first mounting arrangement comprises:
positioning a bite wax impression on the first physical model of the first mounting arrangement; and
positioning the physical model of the second mounting arrangement in accordance with the bite wax impression.

8. The method of claim 1, wherein each bite position includes one selected from the group consisting of a centric occlusion position, a centric relation position, a protrusive position, and a lateral excursion position.

9. The method of claim 1, further comprising determining a third condyle position point corresponding to a third bite position by interpolating points between the first set of positional data and the second set of positional data.

10. The method of claim 1, wherein the first physical model is a cast of teeth of a maxilla of the patient.

11. The method of claim 1, wherein the second physical model is a cast of teeth of a mandible of the patient.

* * * * *